US011471453B2

(12) United States Patent
Rolls et al.

(10) Patent No.: US 11,471,453 B2
(45) Date of Patent: *Oct. 18, 2022

(54) NEURONAL MODULATION

(71) Applicants: TECHNION RESEARCH & DEVELOPMENT FOUNDATION LIMITED, Haifa (IL); HEALTH CORPORATION—RAMBAM, Haifa (IL)

(72) Inventors: Asya Rolls, Haifa (IL); Tamar Ben Shannan, Haifa (IL); Hilla Azulay-Debbie, Haifa (IL); Fahed Hakim, Nazareth (IL); Maya Schiller, Haifa (IL); Shai Shen-Orr, Karkur (IL); Elina Starosvetsky, Yokneam Ilit (IL)

(73) Assignees: TECHNION RESEARCH & DEVELOPMENT FOUNDATION LIMITED, Haifa (IL); HEALTH CORPORATION - RAMBAM, Haifa (IL)

( * ) Notice: Subject to any disclaimer, the term of this patent is extended or adjusted under 35 U.S.C. 154(b) by 81 days.

This patent is subject to a terminal disclaimer.

(21) Appl. No.: 16/834,323

(22) Filed: Mar. 30, 2020

(65) Prior Publication Data
US 2020/0246329 A1 Aug. 6, 2020

Related U.S. Application Data

(63) Continuation of application No. 15/037,412, filed as application No. PCT/IL2014/051026 on Nov. 26, 2014, now Pat. No. 10,603,315.

(60) Provisional application No. 61/908,870, filed on Nov. 26, 2013, provisional application No. 61/908,883, filed on Nov. 26, 2013.

(51) Int. Cl.
| | |
|---|---|
| *A61N 2/00* | (2006.01) |
| *A61N 2/02* | (2006.01) |
| *A61K 31/48* | (2006.01) |
| *A61K 31/428* | (2006.01) |
| *A61K 31/473* | (2006.01) |
| *A61K 31/506* | (2006.01) |
| *A61K 31/404* | (2006.01) |
| *A61K 31/4045* | (2006.01) |

(52) U.S. Cl.
CPC ............ *A61K 31/48* (2013.01); *A61K 31/404* (2013.01); *A61K 31/4045* (2013.01); *A61K 31/428* (2013.01); *A61K 31/473* (2013.01); *A61K 31/506* (2013.01); *A61N 2/006* (2013.01); *A61N 2/02* (2013.01)

(58) Field of Classification Search
CPC . A61N 2/006; A61N 2/02; A61P 37/02; A61P 35/00; A61K 31/404; A61K 31/4045; A61K 31/428; A61K 31/473; A61K 31/48; A61K 31/506
See application file for complete search history.

(56) References Cited

U.S. PATENT DOCUMENTS

| | | | | |
|---|---|---|---|---|
| 5,759,535 | A * | 6/1998 | Cohen .................... | C07K 14/55 424/93.21 |
| 2005/0148808 | A1 | 7/2005 | Cameron et al. | |
| 2006/0058572 | A1 | 3/2006 | Anninou et al. | |
| 2007/0161883 | A1 | 7/2007 | Ayari et al. | |
| 2010/0215674 | A1 | 8/2010 | Thielemans et al. | |
| 2011/0190569 | A1 * | 8/2011 | Simon ...................... | A61N 1/18 600/26 |
| 2013/0079582 | A1 | 3/2013 | Della Rocca et al. | |
| 2014/0358066 | A1 | 12/2014 | Nuccitelli et al. | |
| 2014/0364774 | A1 * | 12/2014 | Mishelevich ............ | A61N 7/02 601/2 |

OTHER PUBLICATIONS

International Search Report and Written Opinion of the International Searching Authority, International Application No. PCT/IL2014/051026, dated Feb. 23, 2015.
Assis et al., Decrease of lymphoproliferative response by amphetamine is mediated by dopamine from the nucleus accumbens: Influence on splenic met-enkephalin levels; Brain, Behavior, and Immunity 25 (2011) 647-657.
Cosentino et al., Human CD4+CD25+ regulatory T cells selectively express tyrosine hydroxylase and contain endogenous catecholamines subserving an autocrine/paracrine inhibitory functional loop; Blood, 2007; 109; 632-642.
Tóth et al., Role of Peripheral and Brain-Derived Dopamine (DA) in Immune Regulation; Advances in Neuroimmune Biology 3 (2012) 111-155.
Ishibashi et al., Inhibition of Growth of Human Small Cell Lung Cancer by Bromocriptine Cancer Research 54, 3442-3446, Jul. 1, 1994.
Tsai et al., Associated Effects of Bromocriptine on Neoplastic Progression of Mouse Mammary Preneoplastic Hyperplastic Alveolar Nodule Line C4 and on Hyperplastic Alveolar Nodule-infiltrating and Splenic Lymphocyte Function, Cancer Research 52, 2209-2215, Apr. 15, 1992.
Hendrickson et al., Modulation of ethanol drinking-in-the-dark by mecamylamine and nicotinic acetylcholine receptor agonists in C57BL/6J mice; Psychopharmacology, 2009, Springer, vol. 204, pp. 563-572.

(Continued)

*Primary Examiner* — Sarah Pihonak
(74) *Attorney, Agent, or Firm* — The Roy Gross Law Firm, LLC; Roy Gross

(57) ABSTRACT

A method for modulating an immune response by activating or inhibiting dopaminergic neurons in the Ventral Tegmental Area (VTA) is provided. Modulation is achieved by modulating the activity, the abundance or both of: a natural killer cell, a CD8 T-cell, a CD4 T-cell, a B-cell, a dendritic cell, a macrophage, a granulocyte, or their combination.

10 Claims, 9 Drawing Sheets
(4 of 9 Drawing Sheet(s) Filed in Color)

(56) References Cited

OTHER PUBLICATIONS

Rogan et al., Remote Control of Neuronal Signaling; Pharmacological Reviews, 2011, vol. 63(2), pp. 291-315.
Wang et al., Dopamine Antagonists and the Development of Breast Cancer, Arch Gen Psych, 2002, vol. 59, pp. 1147-1154.
Wang et al., Cancer risks among the users of ergot-derived dopamine agonists for Parkinson's disease, a nationwide population-based survey, Parkinsonism and Related Disorders, 2015, Elsevier, vol. 21, pp. 18-22.
Yamaguchi et al., Effects of pulsed magnetic stimulation on tumor development and immune functions in mice, Bioelectromagnetics, 2006, Wiley-Liss, vol. 27, pp. 64-72.
Tracey Kevin, The inflammatory reflex, Nature, 2002, Nature Publishing Group, vol. 420, pp. 853-859.
Van Buel, et al., Immune and neurotrophin stimulation by electroconvulsive therapy: is some inflammation needed after all? Transl Psych, 2015, Nature Publishing Group, vol. 5, p. e609.
Elenkov et al., The Sympathetic Nerve—A Integrative Interface between Two Supersystems: The Brain and the Immune System. Pharmacological Reviews, 2000, vol. 52(4), pp. 595-638.
Borovikova, et al., Vagus nerve stimulation attenuates the systemic inflammatory response to endotoxin, Nature, 2000, Nature Publishing Group, vol. 405, pp. 458-462.

\* cited by examiner

Figure 3A
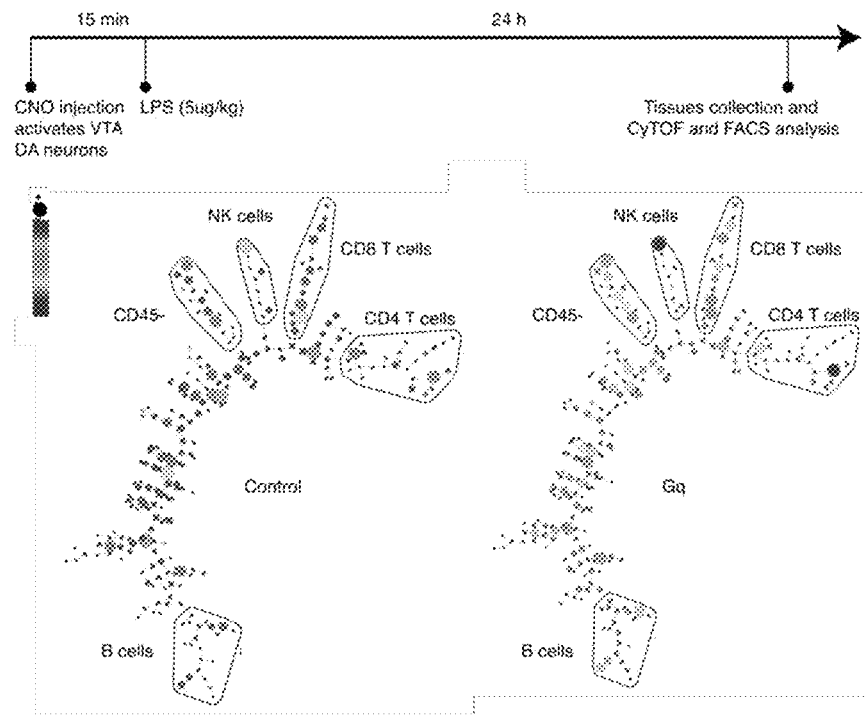
Figure 3B
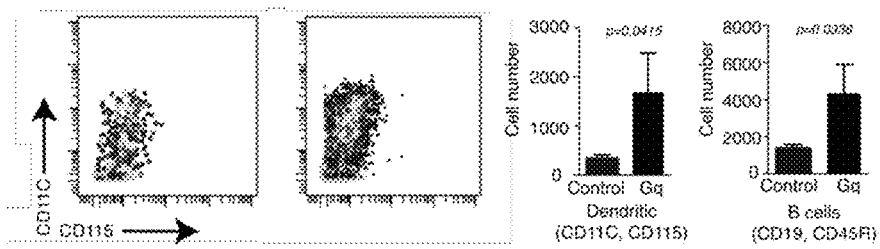
Figure 3C          Figure 3D          Figure 3E

NEURONAL MODULATION

CROSS-REFERENCE TO RELATED APPLICATIONS

This application is a continuation of U.S. patent application Ser. No. 15/037,412, filed on May 18, 2016, which is a National Phase of PCT Patent Application No. PCT/IL2014/051026 having International filing date of Nov. 26, 2014, which claims the benefit of priority of U.S. Provisional Patent Application Nos. 61/908,870 and 61/908,883, both filed on Nov. 26, 2013. The contents of the above applications are all incorporated by reference as if fully set forth herein in their entirety.

FIELD OF THE INVENTION

A method for modulating an immune response and/or treating cancer by activating or inhibiting dopaminergic neurons in the Ventral Tegmental Area (VTA) is provided.

BACKGROUND OF THE INVENTION

Reward is an operational concept used to describe the positive value that an animal attributes to an object, behavior, or internal physical state. The recently development of optogentics, a method that allows for targeted activation of neurons with light (Britt, J. P. & Bonci, A. Optogenetic interrogations of the neural circuits underlying addiction. Current opinion in neurobiology, (2013); Nieh, E. H., Kim, Namburi, P. & Tye, K. M. Optogenetic dissection of neural circuits underlying emotional valence and motivated behaviors. Brain research (2012); and Saunders, B. T. & Richard, J. M. Shedding light on the role of ventral tegmental area dopamine in reward. The Journal of neuroscience : the official journal of the Society for Neuroscience 31, 18195-18197, (2011)), has led to significant advancements in the understanding of the reward system, by enabling dissection of the specific neurons involved in the circuitry, their projections, inputs and specific activation patterns. The reward circuitry is comprised of striatal, limbic, and pre-frontal cortical structures, in which midbrain dopamine (DA) neurons play a critical modulatory role. The VTA receives inputs from the lateral dorsal tegmentum (LDTg), lateral habenula (LHb), lateral hypothalamus (LH) and from the amygdala (Amy). It projects to the nucleus accumbens (NAc), the medial prefrontal cortex (mPFC) and the amygdala. Additional direct and indirect pathways also exist, connecting the various structures comprising the reward system. The specific circuit mediating a defined signal determines the behavioral outcome, as exemplified by the activity of the dopamine neurons in the VTA, which can either induce preference or aversion, depending on the source of the input signal (Lammel, S., Lim, B. K., Ran, C., Huang, K. W. Malenka, R. C. Input-specific control of reward and aversion in the ventral tegmental area. Nature 491, 212-217, (2012)) and the projections that transmit the signal. Deciphering the specific circuits that mediate the effects of the reward system on the immune response is therefore essential to enable manipulations for therapuetic purposes.

While there is significant data suggesting that dopamine directly affects immune cells (Brito-Melo, G., Nicolato, R., de Oliveira, A., Menezes, G., Lelis, F., Avelar, R, Reis, H. Increase in dopaminergic, but not serotoninergic, receptors in T-cells as a marker for schizophrenia severity. Journal of psychiatric research 46, 738-742, (2012); Cosentino, M., Fietta, A. M., Ferrari, M., Rasini, E., Bombelli, R., Carcano, E., Lecchini, S. Human CD4+CD25+ regulatory T cells selectively express tyrosine hydroxylase and contain endogenous catecholamines subserving an autocrine/paracrine inhibitory functional loop. Blood 109, 632-642, (2007); Ferreira, T. B., Kasahara, T. M., Barros, P. O., Vieira, M. M., Bittencourt, V. C., Hygino, J. Bento, C. A. Dopamine up-regulates Th17 phenotype from individuals with generalized anxiety disorder. Journal of neuroimmunology 238, 58-66, (2011); Ilani, T., Strous, R. D. & Fuchs, S. Dopaminergic regulation of immune cells via D3 dopamine receptor: a pathway mediated by activated T cells. FASEB journal: official publication of the Federation of American Societies for Experimental Biology 18, 1600-1602, (2004); Kipnis, J., Cardon, M., Avidan, H., Lewitus, G. M., Mordechay, S., Rolls, A., Schwartz, M. Dopamine, through the extracellular signal-regulated kinase pathway, downregulates CD4+CD25+ regulatory T-cell activity: implications for neurodegeneration. The Journal of neuroscience : the official journal of the Society for Neuroscience 24, 6133-6143, (2004).), the understanding of the central mechanisms, mediated by the dopaminergic network in the brain, is still limited.

Drugs, such as morphine and heroin, which act via dopamine neurons in the VTA, impose an immunosupressive effect (Devoino, L. V., Al'perina, E. L., Gevorgyan, M. M. & Cheido, M. A. Interaction between dopamine D1 and D2 receptors in modulation of the immune response. Bulletin of experimental biology and medicine 141, 553-555 (2006); Devoino, L. V., Al'perina, E. L., Gevorgyan, M. M. & Cheido, M. A. Involvement of dopamine D1 and D2 receptors in the rat nucleus accumbens in immunostimulation. Neuroscience and behavioral physiology 37, 147-151, (2007); Idova, G. V., Alperina, E. L. & Cheido, M. A. Contribution of brain dopamine, serotonin and opioid receptors in the mechanisms of neuroimmunomodulation: evidence from pharmacological analysis. International immunopharmacology 12, 618-625, (2012); Nistico, G., Caroleo, M. C., Arbitrio, M. & Pulvirenti, L. Evidence for an involvement of dopamine D1 receptors in the limbic system in the control of immune mechanisms. Neuroimmunomodulation 1, 174-180 (1994); Szczytkowski, J. L., Lebonville, C., Hutson, L., Fuchs, R. A. & Lysle, D. T. Heroin-induced conditioned immunomodulation requires expression of IL-1beta in the dorsal hippocampus. Brain Behav Immun 30, 95-102, (2013); Simonovska, N., Chibishev, A., Bozinovska, C., Grcevska, L., Dimitrovski, K. & Neceva, V. Evaluation of circulating immune complexes and antiphospholipid antibodies (anti beta 2 glycoprotein 1) in heroin addicts and their clinical significance. Medicinski arhiv 65, 324-326 (2011).), manifested, for example, by decreased NK cell activity, changes in lymphocyte proliferative responses, and nitric oxide production. Part of these effects are mediated via the central nervous system (CNS) as these immunoregulatory effects were shown to depend on the activation of dopamine receptors D(1) and D(2) in specific locations within the NAc (shell vs. core) (Assis, M. A., Valdomero, A., Garcia-Keller, C., Sotomayor, C. & Cancela, L. M. Decrease of lymphoproliferative response by amphetamine is mediated by dopamine from the nucleus accumbens: influence on splenic met-enkephalin levels. Brain Behav Immun 25, 647-657, (2011)).

Transcranial magnetic stimulation (TMS) uses electromagnetic induction to generate an electric current across the scalp and skull without physical contact. A plastic-enclosed coil of wire is held next to the skull and when activated, produces a magnetic field oriented orthogonal to the plane of the coil. The magnetic field passes unimpeded through the skin and skull, inducing an oppositely directed current in the brain that activates nearby nerve cells in much the same way as currents applied directly to the cortical surface (Cacioppo, J T; Tassinary, L G; Berntson, G G., ed. (2007). Handbook of psychophysiology (3rd ed.). New York, N.Y.: Cambridge Univ. Press. p. 121.).

SUMMARY OF THE INVENTION

In one embodiment, this invention provides a method for modulating an immune response in a subject, comprising the step of activating or inhibiting dopaminergic neurons in the Ventral Tegmental Area (VTA) of the subject, thereby modulating an immune response in a subject. In another embodiment, this invention further provides that modulating an immune response is modulating the activity, the abundance or both of a natural killer cell, a CD8 T-cell, a CD4 T-cell, a B-cell, a dendritic cell, a macrophage, a granulocyte, or any combination thereof.

In another embodiment, this invention further provides that modulating and/or activating an immune response is by means of applying magnetic stimulation to the dopaminergic neurons in the Ventral Tegmental Area (VTA).

In another embodiment, this invention further provides a method for treating melanoma and/or carcinoma in a subject, comprising the step of activating dopaminergic neurons in the Ventral Tegmental Area (VTA) of the subject. In another embodiment, activating is increasing the number of: NK cells, B-cells, dendritic cells, macrophages, granulocytes, or any combination thereof in the subject's spleen. In another embodiment, activating is inducing the level and/or abundance of CD62L in CD8 T-cells. In another embodiment, activating is inducing migration of CD8 T-cells.

In another embodiment, the phrase "inducing level and/or abundance" includes inducing the percentage of cells displaying the mentioned (CD) marker in a specific cell group (such as but not limited to: B-cells, granulocytes, macrophages, etc.) In another embodiment, the phrase "inducing level and/or abundance" includes increasing the number of cells displaying the mentioned (CD) marker in a specific cell group (such as but not limited to: B-cells, granulocytes, macrophages, etc.). In another embodiment, the phrase "inducing level and/or abundance" includes inducing the proliferation and/or differentiation of cells displaying the mentioned (CD) marker in a specific cell group (such as but not limited to: B-cells, granulocytes, macrophages, etc.).

In another embodiment, activating is inducing the level and/or abundance of CD1d in granulocytes. In another embodiment, activating is inducing the level and/or abundance of CD1d in macrophage. In another embodiment, activating is inducing the level and/or abundance of CD206 in B-cells. In another embodiment, activating is inducing the level and/or abundance of CD206 in $CD8^+$ T-cells. In another embodiment, activating is inducing the level and/or abundance of CD80 in macrophages. In another embodiment, activating is inducing the level and/or abundance of CD86 in B-cells. In another embodiment, activating is inducing the level and/or abundance of CD69 in macrophages. In another embodiment, activating is inducing the level and/or abundance of CD86 in B-cells. In another embodiment, activating is inducing the level and/or abundance of CD25 in B-cells.

In another embodiment, activating is inducing the level and/or abundance of interferon gamma in T-cells. In another embodiment, activating is inducing the level and/or abundance of interferon gamma in macrophages. In another embodiment, activating is inducing the level and/or abundance of B220 in B-cells. In another embodiment, activating is inducing the level and/or abundance of CD79 in B-cells. In another embodiment, activating is inducing the level and/or abundance of CD19 in B-cells. In another embodiment, activating is inducing the level and/or abundance of CD138 in B-cells.

In another embodiment, this invention further provides a method for modulating an immune response and/or treating melanoma and/or carcinoma in a subject, comprising the step of administering a dopamine agonist configured to cross the blood-brain-barrier or a dopamine antagonist configured to cross the blood-brain-barrier. In another embodiment, the dopamine agonist comprises a D2 agonist activity. In another embodiment, the dopamine antagonist comprises a D2 antagonist activity.

In one embodiment, this invention provides a method for modulating an immune response and/or treating melanoma and/or carcinoma in a subject, comprising the step of activating or inhibiting dopaminergic neurons in the Ventral Tegmental Area (VTA) of the subject with Transcranial magnetic stimulation (TMS) (VTA-TMS).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3E. Are graphs showing the effects of VTA DA neurons activation on a numbers of defined immune populations in the spleen as determined by CyTOF. FIG. 3A is an experimental timeline: spleens were collected from control and Gq mice 24 h after VTA DA activation and LPS injection (5 ug/kg). FIG. 3B. shows cells that were stained with metal conjugated antibodies and passed through a mass spectrometer. The individual ions were counted and then parsed into a flow cytometry file format. This file can be analyzed by traditional flow cytometry software or by SPADE, which allows integrating the complex information. SPADE analysis is composed of several steps: A density-dependent down-sampling of the original data is clustered. Adjacent clusters are drawn in alternating colors. Minimum spanning tree that connects the cell clusters is generated and color-coded. Nodes are colored by the number of cells in each cluster (7-547 cells). This allows visualization of the changes in the various immune populations. Cluster of CD8, CD4, NK B cell and monocytes are indicated. FIG. 3C shows change in the dendritic population positive for CD11C CD115 are shown in dot plot and calibrated in FIG. 3D. FIG. 3E shows a calibration of changes in the number of B (B220+) cells. These results represent only the most significant changes in cell numbers (n=3) Students t-test.

FIG. 5A shows a schematic representation of the injection site and optic fiber location. FIGS. 5B and 5C show fluorsecnt images showing cell-specific ChR2-EYFP expression.

FIG. 6A shows a schematic demonstration of the experimental design. The viral construct used for cre-dependent expression of DREADDs and mCherry, is shown. The control construct does not contain the information for DREADDs. The schematic structure of DREADDs, which are activated by CNO is also shown. Of note, mice in both groups were injected with CNO to control for the potential effects of CNO. FIG. 6B shows a micrograph indicating the injection site (based on Allen Brain Atlas). In the bottom panel, viral expression is indicated by mCherry fluorescence, co-localized with the VTA tyrosine hydroxylase positive neurons (TH+). FIG. 6C is a micrograph showing staining of C-fos and mCherry in the VTA 90 minutes following CNO injection in a VTA-activated mouse. Arrows indicate neurons co-labeled for C-fos and mCherry. FIG. 6D is a bar graph showing quantification of C-fos staining in virus infected cells 90 min after CNO injection. (Shown are means±SD within each group) FIG. 6E is a schematic representation of the CPP paradigm used to evaluate the rewarding effect of VTA dopaminergic neuron activation (detailed in the experimental section). FIG. 6F is a heat map aggregating the location of all mice in each experimental group (VTA activated or control) in the CPP apparatus during the test session, performed on day 4. VTA-activated mice show a strong preference towards the chamber in which they were injected with CNO, whereas control mice traveled between the two chambers, spent more time in the chamber corners and as a group, did not show a clear preference to any single chamber. FIG. 6G is a bar graph showing quantification of the proportion of time spent in the conditioning chamber on the test session (day 4) relative to the pre-test (day 1). n=8 mice per group; student's t-test ($p<=0.042$).

FIG. 7A is a schematic representation of the high dimensional immune analysis procedure. Blood and spleen from VTA-activated mice were subject to high dimensional analysis by CyTOF mass cytometry and multiplex serum cytokine analysis. FIG. 7B is a cell subset frequency table and map showing changes between the VTA activated mice and their controls following VTA-dopaminergic neurons activation. The 151 identified cell clusters are represented as nodes in a Citrus derived circular dendrogram delineating lineage relationships as identified from the data. Individual cell clusters are mapped to well established, gross-cell types (Bcells; CD45R+/CD79b+, plasma cells; CD45R+/CD79b+/CD138+, CD8+ T-cells; TCRb+/CD8+, CD4+ Tcells: TCRb+/CD4+, NK cells: NK1.1+/CD49b+, granulocytes: CD11b+/Gr1+, monocytes/macrophages (CD11b+/CD14+/F4/80+), uncharacterized: CD45R+/CD79b+/CD138+/NK1.1+/CD14+/CD115+/CD 133+/CD34+), identifiable by annotated shaded grey background groupings. Cluster granularity (i.e. cell subset specificity) increases from the center of the diagram (filled grey nodes representing the aggregate of all measured cells) to the periphery. Cell clusters whose abundance differs in blood or spleen between VT activated and control mice groups are filled orange or circled blue, respectively. Boxplots showing percent cluster frequency of top encompassing cluster in each lineage different between groups are displayed (n=5 per group). FIG. 7C shows a blood cell clusters table and map of APCs of VTA-activated mice show decreased expression of CD1d. Shown is a sector of the Citrus circular dendrogram corresponding to granulocytes, NK, dendritic cells and macrophage/monocytes. Cell clusters downregulating CD1d are colored filled. Inset shows histogram of CD1d expression in top monocyte cell cluster (arrow) of VTA-activated vs. control mice. FIG. 7D is a map showing the differences in functional markers expression for cell clusters in spleen of VTA activated and control mice are indicated for each cell cluster. One or more colored rings, corresponding to different functional markers, circle cell clusters in which the median expression is different between the two experimental groups. Inset: histograms of antigen presentation related functional markers expression difference between groups are shown for the boxed macrophage/monocyte cluster. FIG. 7E are bar graphs showing IL-4 and IL-1β quantitative ELISA analysis of VTA-activated and control mice serum. Student's t-test for IL-4 and IL-1β (IL-4: $p<=0.045$; IL-1β: $p<=0.041$).

FIG. 8A is representative samples of agar plates from each experimental group. FIG. 8B is a micrograph showing quantification of the number of remaining bacteria following incubation with monocytes/macrophages derived from each experimental group (n=5 $p<=0.026$; Student's t-test.) FIG. 8C are activity maps taken twenty four hours following the activation of VTA dopaminergic neurons, mice were injected with GFP-expressing *E. coli* and the number of GFP+ monocytes/macrophages in the peritoneum was analyzed two hour later. A representative dot blot of CD11b-positive cells co-expressing GFP is shown. FIG. 8D is a bar graph showing quantification of GFP+ cells co-labeled for CD11b. n=4-6 mice per group. Student's t-test (p<=0.003).

FIG. 9A is a schematic demonstration of the experimental design. Thirty days after VTA virus injection, mice were injected twice with 6-OHDA (150 mg/kg) at 24 h interval. Five days after the last 6-OHDA injection, VTA dopaminergic neurons were activated with CNO. Twenty-four hours later spleens were removed and processed for CyTOF analysis (FIG. 11). FIG. 9B is a bar graph showing in-vitro *E. coli* killing assay. Four groups of mice were included in the experiment: mice with intact SNS (VTA-activated and control) and mice treated with 6-OHDA (VTA-activated and control) (n=4 per group). Monocytes/macrophages were isolated from the spleens of mice in all experimental groups 24 h following VTA-activation. The cells were then co-cultured with *E. coli* for four hours, lysed and plated on agar. Quantification of the number of remaining bacteria following incubation with monocytes/macrophages derived from each experimental group (n=4-6 per group; p<=0.93).

FIG. 11A is a map showing cell subset frequency changes following VTA dopaminergic neurons activation. Cell clusters are represented as nodes in a circular dendrogram delineating lineage relationships as identified from the data. Individual cell clusters are mapped to well established, gross-cell types, identifiable by annotated shaded grey background groupings, with cluster granularity (i.e. cell subset specificity) increases moving from the center of the diagram (filled grey node) to the periphery. FIG. 11B is a histogram showing CD45 levels in the total population of analyzed cells and in the indicated cluster. FIG. 11C a boxplot of the indicated cluster (arrow) is shown (n=4 per group). DFR was set at 10% and yet no other differences were detectable.

FIG. 12B shows high-magnification demonstrating the colocalization between the hM3D(Gq)-mCherry and TH.

FIG. 13A is a scheme of the experiment design. CNO (required for VTA activation-Gq group) was injected daily for two sessions of three days each (separated by seven day intervals; total of six days). CNO injections started immedia-tely with the injection of tumor cells. FIG. 13B is a bar graph showing tumor weight (determined. Student's t-test p=0.05. n=5 per group).

DETAILED DESCRIPTION OF THE INVENTION

Figure 1:
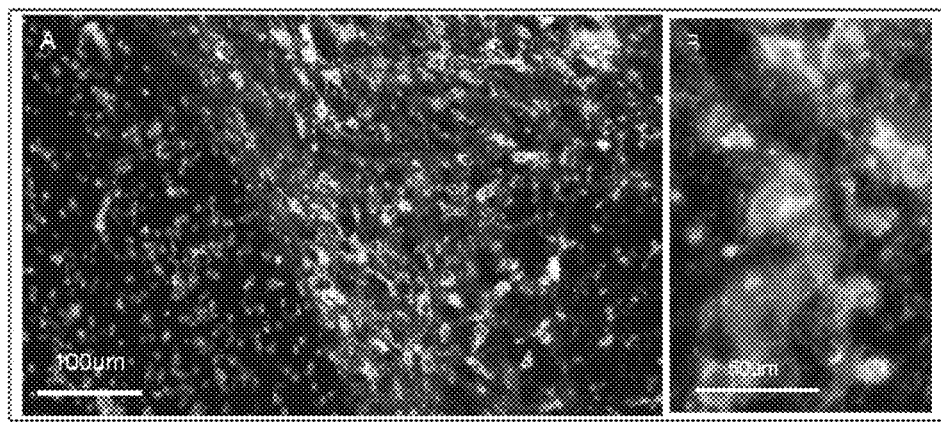
FIG. 1. Is a micrograph showing the specificity of virus expression in TH+neurons of the VTA. (A) Cre-dependent AAV (expressing hM3D(Gq)-mCherry) was injected into the VTA. Fluorescent microscope image of an injected slice demonstrates colocalization of mCherry expression with the TH antibody, costained with 4′,6′-diamidino-2-phenylindole (DAPI). (B) High-magnification demonstrating the colocalization between the hM3D(Gq)-mCherry and TH staining.

The present invention provides, in one embodiment, a method for modulating an immune response in a subject, comprising the step of activating or inhibiting dopaminergic neurons in the Ventral Tegmental Area (VTA) of the subject, thereby modulating an immune response in a subject. In another embodiment, modulating an immune response is increasing, inducing, elevating, activating, differentially activating, or any combination thereof, an immune response. In another embodiment, modulating an immune response is decreasing, inhibiting, differentially inhibiting, or any combination thereof, an immune response.

In another embodiment, the present invention provides that VTA dopaminergic neurons alter an immune response. In another embodiment, the present invention provides that VTA dopaminergic neurons alter an immune response in a specific and homeostatic manner. In another embodiment, the present invention provides that VTA neuronal activation increases the number of NK cells B-cells and CD11C+ CD115+ dendritic cells in the spleen. In another embodiment, the present invention provides that VTA neuronal activation increases the level of CD62L, a migration-guiding molecule, on subsets of CD8 T cells (FIG. 1-4), but have no effect on the level of the cell activation marker CD69.

In another embodiment, the term "modulating" is altering. In another embodiment, the term "modulating" is activating. In another embodiment, the term "modulating" is inhibiting. In another embodiment, the term "modulating" is increasing. In another embodiment, the term "modulating" is inducing. In another embodiment, the term "modulating" is elevating. In another embodiment, the term "modulating" is reducing. In another embodiment, the term "modulating" is differentially activating. In another embodiment, the term "modulating" is decreasing. In another embodiment, the term "modulating" is inhibiting. In another embodiment, the term "modulating" is differentially inhibiting. In another embodiment, modulating an immune response includes the activation and/or induction of certain immune cells or sub-sets, while at the same time inhibiting other immune cells or particular sub-sets immune cells.

In another embodiment, an immune response is any response taken by the body to defend itself from pathogens or abnormalities. In another embodiment, an immune response is any response is activating or inhibiting the immune system or mediators of the immune system. In another embodiment, an immune response is activation of an immune cell. In another embodiment, activation of an immune cell results in the proliferation of a sub-set of immune cells. In another embodiment, activation of an immune cell results in increase secretion of immunologic mediators by the activated cell. In another embodiment, activation of an immune cell results in the engulfment and or destruction of a pathogen or a foreign cell or molecule. In another embodiment, activation of an immune cell results in the engulfment and or destruction of a neighboring cell such as but not limited to a cell infected by a virus.

In another embodiment, an immune response is any response activating or inhibiting: B-cells, Dendritic cells, macrophages, Natural Killer (NK) cells, T-cells, Thymocytes, or any combination thereof In another embodiment, a response activating or inhibiting a cell as described herein, results: in the proliferation of the cell or another immune cell, in inhibiting the proliferation of the cell or another immune cell, in the secretion of immune mediators such as cytokines, in the migration of an immune cell, in the activation of an immune cascade, in the elimination of foreign molecules or cells, or any combination thereof.

In another embodiment, an immune response is associated with a disease and a method described herein is used to optimize the immune response according to the exact condition. In another embodiment, the disease is an autoimmune disease. In another embodiment, the disease is Addison's disease. In another embodiment, the disease is Celiac. In another embodiment, the disease is Dermatomyositis. In another embodiment, the disease is Graves disease. In another embodiment, the disease is Hashimoto's thyroiditis. In another embodiment, the disease is Multiple sclerosis. In another embodiment, the disease is Myasthenia gravis. In another embodiment, the disease is Pernicious anemia. In another embodiment, the disease is Reactive arthritis. In another embodiment, the disease is Rheumatoid arthritis. In another embodiment, the disease is Sjogren syndrome. In another embodiment, the disease is Systemic lupus erythematosus. In another embodiment, the disease is Type I diabetes.

In another embodiment, the disease is an immune system disorder. In another embodiment, an immune system disorder is associated with abnormally low activity or overactivity of the immune system. In cases of immune system overactivity, the body attacks and damages its own tissues (autoimmune diseases). In another embodiment, the disease is an immune deficiency disease such as AIDS. In another embodiment, the disease is an allergy. In another embodiment, the disease is asthma. In another embodiment, the disease is an inflammatory disease.

In another embodiment, an immune response is associated with a vaccine and a method described herein is used to optimize vaccination and the immune response associated with same. In another embodiment, an immune response is associated with cancer therapy wherein an immune response is triggered against tumor/cancer cells or cancer/tumor antigens. In another embodiment, methods and composition if the invention for modulating an immune response have direct positive impact on cancer therapy.

In one embodiment, the present invention provides composition and methods for treating cancer wherein the methods/compositions activate VTA neurons. In another embodiment, cancer treatable by the methods (such as TMS) and/or compositions as described herein is melanoma. In another embodiment, cancer treatable by the methods (such as TMS) and/or compositions as described herein is carcinoma. In another embodiment, cancer treatable by the methods (such as TMS) and/or compositions as described herein is Solid melanoma. In another embodiment, cancer treatable by the methods (such as TMS) and/or compositions as described herein is lung carcinoma. In another embodiment, cancer treatable by the methods (such as TMS) and/or compositions as described herein includes tumors. In another embodiment, cancer treatment includes means for inhibiting the growth of a tumor. In another embodiment, cancer treatment includes means for inhibiting metastasis.

In another embodiment, cancer treatable by the methods (such as TMS) and/or compositions as described herein is: adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell, lymphoma, AIDS-related, lymphoma, central nervous system (primary), lymphoma, cutaneous T-cell, lymphoma, hodgkin's disease, non-hodgkin's disease, malignant mesothelioma, melanoma, merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, sezary syndrome, skin cancer, cutaneous T-cell lymphoma, skin cancer, kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, or wilms' tumor.

In another embodiment, a subject is a human subject. In another embodiment, a subject is a farm animal. In another embodiment, a subject is a pet. In another embodiment, a subject is a lab animal. In another embodiment, a subject is a rodent.

In another embodiment, dopaminergic neurons are found in the substantia nigra pars compacta of the brain. In another embodiment, dopaminergic neurons are found in the ventral tegmental area (VTA) in the midbrain. In another embodiment, dopaminergic neurons use the neurotransmitter dopamine as a relay.

In another embodiment, the ventral tegmental area of Tsai (VTA) is the origin of the dopaminergic cell bodies of the mesocorticolimbic dopamine system. In another embodiment, neurons of the invention project to the prefrontal cortex. In another embodiment, neurons of the invention project to the caudal brainstem. In another embodiment, neurons of the invention project to any brain region between the prefrontal cortex and the caudal brainstem. In another embodiment, neurons of the invention are melanin-pigmented dopaminergic neurons. In another embodiment, neurons of the invention are GABAergic neurons. In another embodiment, neurons of the invention are excitatory glutamatergic neurons. In another embodiment, the VTA dopaminergic neurons of the present invention are neurons projecting to the prefrontal cortex, NAc and amygdala.

In another embodiment, modulating an immune response is modulating the activity, the abundance or both of a natural killer cell, a CD8 T-cell, a CD4 T-cell, a B-cell, a dendritic cell, a basophil, a mast cell, an eosinophil, a plasma cell, an antigen presenting cell (APC), a platelet, a macrophage, a granulocyte or any combination thereof. In another embodiment, modulating the activity is priming an immune cell towards a specific target. In another embodiment, modulating the activity is elevation in blood, spleen and/or bone marrow B-cell count. In another embodiment, modulating the activity of a certain cell is inducing the cell's activity. In another embodiment, modulating the activity is inducing imuune cell proliferation and/or differentiation.

In another embodiment, the invention provides activating dopaminergic neurons in the VTA of the subject. In another embodiment, activating dopaminergic neurons in the VTA of the subject results in induction of proliferation of NK cells. In another embodiment, activating dopaminergic neurons in the VTA of the subject results in increase of NK cells number. In another embodiment, activating dopaminergic neurons in the VTA of the subject results in induction of proliferation of B-cells. In another embodiment, activating dopaminergic neurons in the VTA of the subject results in increase of B-cells number. In another embodiment, activating dopaminergic neurons in the VTA of the subject results in proliferation induction of dendritic cells. In another embodiment, activating dopaminergic neurons in the VTA of the subject results in increase of dendritic cells number. In another embodiment, activating dopaminergic neurons in the VTA of the subject results in proliferation induction of immune cells in the spleen. In another embodiment, activating dopaminergic neurons in the VTA of the subject results in elevated migration of CD8 T-cells. In another embodiment, activating dopaminergic neurons in the VTA of the subject results in increase of the level of CD62L in CD8 T-cells.

In another embodiment, modulating is administering a modulator of an immune response. In another embodiment, a modulator of an immune response comprises a D2 agonist activity or a D2 antagonist activity.

In another embodiment, a modulator of an immune response or a compound that activates VTA neurons is a compound that is blood-brain-barrier (BBB) permeable. In another embodiment, a modulator of an immune response or a compound that activates VTA neurons is a compound that can penetrate the BBB, by itself or via a carrier. In another embodiment, a modulator of an immune response or a compound that activates VTA neurons is a compound that is attached to or entrapped within a carrier that is BBB permeable. In another embodiment, carriers that are BBB permeable are known to a person of skill in the art and include: nanoparticles, nanocapsules, lyposomes, BBB penetrating peptides, or any combination thereof.

In another embodiment, activation of VTA neurons can be performed by any method known to one of skill in the art. In another embodiment, activation of VTA neurons can be performed by a pharmacologic agent, a magnetic and/or an electric stimulation, an ultrasound, or any combination thereof.

In another embodiment, VTA neurons are activated by synthetic ligand (RASSLs). In another embodiment, VTA neurons are activated by transfecting VTA neurons with designer receptors exclusively activated by designer drug (DREADDs). In another embodiment, VTA neurons are activated by transfecting VTA neurons with hM3D (Gq) or hM4D (Gi) by any suitable vector known to one of skill in the art. In another embodiment, VTA neurons expressing DREADDs are activated by clozapine-N-oxide (CNO). In another embodiment, VTA neurons expressing DREADDs are activated by clozapine-N-oxide (CNO) at a dosage of between 0.1 to 20 mg/kg. In another embodiment, VTA neurons expressing DREADDs are activated by clozapine-N-oxide (CNO) at a dosage of between 1 to 5 mg/kg.

In another embodiment, a modulator of an immune response is a dopamine agonist. In another embodiment, the dopamine agonist is Lisuride. In another embodiment, a dopamine agonist is an Adamantane. In another embodiment, a dopamine agonist is an Aminotetralin. In another embodiment, a dopamine agonist is a Benzazepine. In another embodiment, a dopamine agonist is an Ergoline. In another embodiment, a dopamine agonist is a Dihydrexidine derivative. In another embodiment, a dopamine agonist is an ergot derivative such as Bromocriptine.

In another embodiment, a dopamine agonist is Ropinirole. In another embodiment, a dopamine agonist is Pramipexole. In another embodiment, a dopamine agonist is Pergolide. In another embodiment, a dopamine agonist is Lisuride. In another embodiment, a dopamine agonist is Cabergoline. In another embodiment, a dopamine agonist is A-68,930. In another embodiment, a dopamine agonist is A-77,636. In another embodiment, a dopamine agonist is A-412,997. In another embodiment, a dopamine agonist is ABT-670. In another embodiment, a dopamine agonist is ABT-724. In another embodiment, a dopamine agonist is Aplindore. In another embodiment, a dopamine agonist is Apomorphine. In another embodiment, a dopamine agonist is Aripiprazole. In another embodiment, a dopamine agonist is Bifeprunox. In another embodiment, a dopamine agonist is BP-897. In another embodiment, a dopamine agonist is CY-208,243. In another embodiment, a dopamine agonist is Dizocilpine. In another embodiment, a dopamine agonist is Etilevodopa. In another embodiment, a dopamine agonist is Flibanserin. In another embodiment, a dopamine agonist is Ketamine. In another embodiment, a dopamine agonist is Melevodopa. In another embodiment, a dopamine agonist is Modafinil. In another embodiment, a dopamine agonist is Pardoprunox. In another embodiment, a dopamine agonist is Phencyclidine. In another embodiment, a dopamine agonist is PD-128,907. In another embodiment, a dopamine agonist is PD-168,077. In another embodiment, a dopamine agonist is PF-219,061. In another embodiment, a dopamine agonist is Piribedil. In another embodiment, a dopamine agonist is Pramipexole. In another embodiment, a dopamine agonist is Propylnorapomorphine. In another embodiment, a dopamine agonist is Pukateine. In another embodiment, a dopamine agonist is Quinagolide. In another embodiment, a dopamine agonist is Quinelorane. In another embodiment, a dopamine agonist is Quinpirole. In another embodiment, a dopamine agonist is RDS-127. In another embodiment, a dopamine agonist is Ro10-5824 In another embodiment, a dopamine agonist is Ropinirole. In another embodiment, a dopamine agonist is Rotigotine. In another embodiment, a dopamine agonist is Roxindole. In another embodiment, a dopamine agonist is Salvinorin. A In another embodiment, a dopamine agonist is SKF-89,145. In another embodiment, a dopamine agonist is Sumanirole In another embodiment, a dopamine agonist is Terguride. In another embodiment, a dopamine agonist is Umespirone. In another embodiment, a dopamine agonist is WAY-100,635.

In another embodiment, a modulator of an immune response is a dopamine antagonist. In another embodiment, a dopamine antagonist is a typical antipsychotic such as: Acepromazine, Azaperone, Benperidol, Bromperidol, Clopenthixol, Chlorpromazine, Chlorprothixene, Droperidol, Flupentixol, Fluphenazine, Fluspirilene, Haloperidol, Loxapine, Mesoridazine, Methotrimeprazine, Nemonapride, Penfluridol, Perazine, Periciazine, Perphenazine, Pimozide, Prochlorperazine, Promazine, Sulforidazine, Sulpiride, Sultopride, Thioridazine, Thiothixene, Trifluoperazine, Triflupromazine, Trifluperidol, or Zuclopenthixol. In another embodiment, a dopamine antagonist is an atypical antipsychotic such as: Amisulpride, Asenapine, Blonanserin, Cariprazine, Carpipramine, Clocapramine, Clozapine, Gevotroline, Iloperidone, Lurasidone, Melperone, Molindone, Mosapramine, Ocaperidone, Olanzapine, Paliperidone, Perospirone, Piquindone, Quetiapine, Remoxipride, Risperidone, Sertindole, Tiospirone, Ziprasidone, or Zotepine. In another embodiment, a dopamine antagonist is: Amoxapine, Buspirone, Butaclamol, Ecopipam, N-Ethoxycarbonyl-2-ethoxy-1,2-dihydroquinoline (EEDQ), Eticlopride, Fananserin, L-745,870, Nafadotride, Nuciferine, PNU-99,194, Raclopride, Sarizotan, SB-277,011-A, SCH-23,390, SKF-83,566, SKF-83,959, Sonepiprazole, Spiperone, Spiroxatrine, Stepholidine, Tetrahydropalmatine, Tiapride, UH-232, or Yohimbine.

In another embodiment, modulating is by means of magnetic stimulation using induced currents. In another embodiment, TMS is a time-varying pulse of current in an external coil causing inducing currents in the brain. In another embodiment, magnetic stimulation is used for electrical stimulation of nerves in the VTA. In another embodiment, depolarization of nerves by TMS includes a rise time of order 100 μsec, a peak field of order 1 Tesla and magnetic field energy of several hundred joules. In another embodiment, magnetic field pulses are generated with with peak coil currents in the range of several kiloamps and discharge voltages of up to a few kilovolts.

In another embodiment, TMS can be substituted with cranial electrotherapy stimulation. In another embodiment, TMS can be substituted with transcranial direct current stimulation. In another embodiment, TMS can be substituted with electroconvulsive therapy.

In another embodiment, a TMS of the invention includes stimulating coil geometry of a circle or a 'figure-of-eight'. In another embodiment, a TMS of the invention run at tens of stimuli per second. In another embodiment, TMS stimulation is delivered to a single cortical target using the same coil. In another embodiment, multiple stimuli of TMS are delivered in trains. In another embodiment, 'high-frequency' rTMS is utilized according to the invention. In another embodiment, a theta burst (TBS) protocol providing short bursts of 50 Hz rTMS is used at a rate in the theta range (5 Hz) as a continuous (cTBS), or intermittent (iTBS) train. In another embodiment, quadripulse stimulation (QPS) is applied (patterned rTMS procedure able to induce long-term changes of cortical excitability).

In another embodiment, a TMS includes a coil for magnetic stimulation positionable on a head part. In another embodiment, a TMS includes a coil for magnetic stimulation positionable on a head part for stimulating a deep brain region. In another embodiment, the coils are oriented such that they will produce a considerable field in a direction tangential to the surface, which should also be the preferable direction to activate the VTA neurons. In another embodiment, the wires of the coils are directed in one or more directions, which results in a preferred activation of VTA neuronal structures. In another embodiment, deep TMS according to the invention provide deep region stimulation without causing a large electrical field at surface areas of the brain.

In another embodiment, the invention provides a method for activating dopaminergic neurons in the Ventral Tegmental Area (VTA) of the subject by magnetic stimulation. In another embodiment, the invention provides a method for activating dopaminergic neurons in the Ventral Tegmental Area (VTA) of the subject by magnetic stimulation with Transcranial magnetic stimulation (TMS) (VTA-TMS). In another embodiment, the invention provides a method for activating an immune response or treating cancer, and/or inhibiting the growth of a tumor, comprising the step of activating dopaminergic neurons in the Ventral Tegmental Area (VTA) of the subject by magnetic stimulation with Transcranial magnetic stimulation (TMS) (VTA-TMS).

In another embodiment, TMS and methods of using TMS are described and disclosed in U.S. Pat. No. 8,771,163 (Transcranial magnetic stimulation system and methods); U.S. Pat. No. 8,388,510 (Transcranial magnetic stimulation system and methods); U.S. Pat. No. 8,277,371 (Transcranial magnetic stimulation system and methods; U.S. Pat. No. 7,976,451 (Transcranial magnetic stimulation system and methods) are herein incorporated by reference in their entirety. In another embodiment, the TMS disclosed in International Publication Number WO 02/32504 is herein incorporated by reference in its entirety.

In another embodiment, activating dopaminergic neurons in the Ventral Tegmental Area (VTA) involves stimulating deep brain regions using TMS. In another embodiment, TMS is a system including a coil holder (such as a helmet). In another embodiment, a coil holder is positionable around a head of a subject. In another embodiment, TMS includes an electrical stimulator (such as a neurostimulator) connected to the coils. In another embodiment, the stimulator provides a controlled output, frequency, and pulse duration.

In another embodiment, a method such as described herein involves a predetermined number of trains with TMS. In some embodiments, a train of 1 to 100 pulses is administered. In some embodiments, a train of 1 to 50 pulses is administered. In some embodiments, a train of 20 to 80 pulses is administered.

In another embodiment, each is from 50 to 2000 microseconds. In another embodiment, each is from 100 to 1200 microseconds. In another embodiment, each is from 500 to 1500 microseconds. In another embodiment, each is from 800 to 1200 microseconds. In another embodiment, the duration of each train is 0.1 to 5 seconds, with an inter-train interval of 1 to 200 seconds. In another embodiment, the duration of each train is 0.5 to 2 seconds, with an inter-train interval of 5 to 50 seconds. In another embodiment, the duration of each train is 0.5 to 2 seconds, with an inter-train interval of 10 to 30 seconds. In another embodiment, the pulses are in the range of 1 to 100 Hz In another embodiment, the pulses are in the range of 1 to 30 Hz In another embodiment, the pulses are in the range of 50 to 100 Hz In another embodiment, the pulses are in the range of 20 to 70 Hz.

In another embodiment, the TMS system provides several sub-threshold impulses. In one embodiment of the present invention, a different type of spatial summation is contemplated. In another embodiment, several points along a neuronal structure are stimulated.

In another embodiment, the coordinates for stimulating the VTA region with TMS are known to one of skill in the art. In another embodiment, stimulating with TMS the VTA region include the following positioning of the coil: −1.0 to 5.4; −18 to −14; −13 to −7. In another embodiment, stimulating with TMS the VTA region include the following positioning of the coil: −0.5 to 4.5; −16 to −15; −10 to −9. In another embodiment, stimulating with TMS the VTA region include the following positioning coordinates of the coil: 0; −15; −9. In another embodiment, stimulating with TMS the VTA region include the following positioning coordinates of the coil: 4; −16; −10. In another embodiment, the first coordinate is anterior-posterior. In another embodiment, the second coordinate is media-lateral. In another embodiment, the third coordinate is dorsal-ventral. In another embodiment, the units are in centimeters.

In another embodiment, this invention further provides that modulating and/or activating an immune response by means of applying magnetic stimulation to the dopaminergic neurons in the Ventral Tegmental Area (VTA), is modulating the activity, the abundance or both of: a natural killer cell, a CD8 T-cell, a CD4 T-cell, a B-cell, a Dendritic cell, or any combination thereof.

In another embodiment, this invention further provides a method for activating an immune response in a subject, comprising the step of activating dopaminergic neurons in the Ventral Tegmental Area (VTA) of the subject, thereby activating an immune response in a subject. In another embodiment, activating is increasing the number of: NK cells, B-cells and dendritic cells in the subject's spleen. In another embodiment, activating is inducing the level of CD62L in CD8 T-cells. In another embodiment, activating is inducing migration of CD8 T-cells.

In another embodiment, this invention further provides a method for modulating an immune response in a subject, comprising the step of administering a dopamine agonist configured to cross the blood-brain-barrier or a dopamine antagonist configured to cross the blood-brain-barrier. In another embodiment, the dopamine agonist comprises a D2 agonist activity. In another embodiment, the dopamine antagonist comprises a D2 antagonist activity.

In one embodiment, this invention provides a method for modulating an immune response in a subject, comprising the step of activating or inhibiting dopaminergic neurons in the Ventral Tegmental Area (VTA) of the subject with Transcranial magnetic stimulation (TMS) (VTA-TMS), thereby modulating an immune response in a subject. In another embodiment, this invention further provides that modulating an immune response with VTA-TMS is modulating the activity, the abundance or both of a natural killer cell, a CD8 T-cell, a CD4 T-cell, a B-cell, a Dendritic cell, or any combination thereof.

In another embodiment, this invention further provides a method for activating an immune response in a subject, comprising the step of activating dopaminergic neurons with VTA-TMS, thereby activating an immune response in a subject. In another embodiment, activating is increasing the number of: NK cells, B-cells and dendritic cells in the subject's spleen. In another embodiment, activating is inducing the level of CD62L in CD8 T-cells. In another embodiment, activating is inducing migration of CD8 T-cells.

In another embodiment, a modulator of the invention that acts within the VTA is administered in a composition and in a dose range that minimizes its psycho-activity. In another embodiment, a modulator of the invention that acts within the VTA is administered in a composition and in a dose range that minimizes side effects such as but not limited to: psychosis, Euphoria, Pericardial effusion, fibrotic reactions, Hallucinations, Orthostatic hypotension, increased orgasmic intensity, Anorexia, Nausea/vomiting, insomnia, dizziness, drowsiness, lightheadedness, Raynaud's phenomenon, syncope, twitching, twisting, or other unusual body movements, or pathological addiction.

In another embodiment, a modulator of the invention is administered to a subject in need of an immune response modulation in combination with at least one immune modulator that does not act within the brain.

In one embodiment, the modulator of the present invention can be provided to the individual per se. In one embodiment, the modulator of the present invention can be provided to the individual as part of a pharmaceutical composition where it is mixed with a pharmaceutically acceptable carrier.

In one embodiment, a "pharmaceutical composition" refers to a preparation of one or more of the modulators described herein with other chemical components such as physiologically suitable carriers and excipients. The purpose of a pharmaceutical composition is to facilitate administration of a modulator to an organism.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease or immune response, severity of a disease, age, sex, or body weight as can be readily made by a person skilled in the art.

In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered modulator. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979)).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Oral administration, in one embodiment, comprises a unit dosage form comprising tablets, capsules, lozenges, chewable tablets, suspensions, emulsions and the like. Such unit dosage forms comprise a safe and effective amount of the desired modulator, or modulators. The pharmaceutically-acceptable carriers suitable for the preparation of unit dosage forms for peroral administration are well-known in the art.

In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjutants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets.

In some embodiments, compositions for use in the methods of this invention comprise solutions or emulsions, which in some embodiments are aqueous solutions or emulsions comprising a safe and effective amount of the modulator of the present invention and optionally, other compounds.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In another embodiment, a modulator is delivered in a vesicle, in particular a liposome (see Langer, Science 249: 1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In one embodiment, compositions of the present invention are presented in a pack or dispenser device, such as an FDA approved kit, which contain one or more unit dosage forms containing the modulator. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the modulator of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

EXAMPLES

Material and Methods
Animals

Mice were anesthetized using a ketamine/xylazine mixture (ketamine 80 mg/kg; xylazine 15-20 mg/kg) diluted in sterile saline solution (NaCl 0.9%), before being fixed in the stereotactic frame (Stoelting, Ill., US). The AAV8 virus, purchased from the vector core at the University of North Carolina, was used to induce Cre-dependent DREADD expression (AAV8-hSyn-DIO-hM3D(Gq)-mCherry), by injection of 0.7 μl into the right VTA region (anterior-posterior −3.2 mm; media-lateral 0.48 mm; dorsal-ventral 4.7 mm (mouse coordinates)). Control mice were injected with a sham AAV8-hSyn-DIO-mCherry construct which did not carry the information for DREADD. 30 days post surgery passed in order to assure the expression of DREADDs. Stereotaxic injection sites were verified by immunohistochemistry and only mice with at least 50% of their TH+ cells co-expressing mCherry were included in the study.

Behavioral Procedure

All behavioral tests were conducted during the same circadian period. The conditional place preference (CPP) test was performed in a rectangular cage with two chambers (25 cm×25 cm each), with a corridor (5 cm×5 cm) connecting the two chambers. The chambers differed in their visual cues and were designed so that mice will have no bias for a particular chamber. The CPP paradigm consisted of four sessions over four days and was conducted 30 days after the viral stereotactic injection. On day 1, individual mice were placed in the connecting corridor (in the same direction) and allowed to freely explore the entire apparatus for 15 minutes (pre-test). On day 2, mice were IP injected with CNO (2.5 mg/kg, Sigma-Aldrich) diluted in sterile saline in order to activate the VTA dopaminergic neurons and then the mice were confined to one of the chambers for 30 min. On day 3, mice were confined to the other chamber for 30 min, 10 min after an injection of sterile saline. On day 4, mice were placed in the center chamber and allowed to freely explore the entire apparatus for 15 minutes (post-test). To calculate the level of preference, the relative time (%) the mouse spent during post-test in the conditioned chamber (the chamber where it received the CNO injection) was divided by the relative time (%) the mouse spent in this chamber during the pre-test (post/pre ratio). Of note, mice in both groups were injected with CNO to control for the potential effects of CNO. The analysis was performed automatically using EthoVision software.

Tissue Preparation and Immunohistochemistry

Validation of the virus injection site and evaluation of the DREADDs expression were performed by immunohistochemistry. Mice were sacrificed and their brains were fixed in 4% paraformaldehyde (PFA) in PBS for 48 hours, cryoprotected in 30% sucrose solution for another 48 hours and then frozen in a metal beaker containing Isopentane and placed in a dewar of liquid nitrogen. Coronal cryosections from the midbrain were sliced at 12 μm thickness and mounted on super-frost slides (Fisherbrand). The tissues were stained for TH with mouse anti-TH (1:200; Millipore) and the proportion of the DREADDs expressing cells (mCherry+) out of the total TH+ in the VTA was evaluated (1800 cells). To evaluate c-fos expression, the mouse brains were examined 90 minutes after CNO injection. After fixation and cryoprotection the brains were frozen. Midbrain coronal 10 μm sections were prepared and stained with rabbit anti c-fos antibodies (1:100, Calbiochem, US). The proportion of the c-fos+ cell nuclei from the total number of DREADDs-expressing cells was calculated. All images were taken as z-stack fluorescent ×20 magnification images using an LSM 700 confocal microscope (Zeiss). The quantification of double-positive cells was performed using Imaris Software.

Mass Cytometry Measurement and Analysis

Two weeks after completion of the behavioral testing, mice were injected intraperitoneally with CNO and anesthetized 24 hours thereafter. Spleens and blood samples were collected. Spleens were dissociated into single-cell suspensions in 2% fetal bovine serum (Biological Industries, IL) and mesh filtered to remove clumps and debris. Blood samples were collected into heparin-coated sterile test tubes. Both the blood and the spleen cell suspensions were lysed with red blood cell lysis buffer (BD Biosciences, NJ, US). Cells ($2 \times 10^6$) from each tissue were stained, for 1 hour at room temperature, with a mixture of metal tagged antibodies recognizing CD45, CCR3, CD80, GR1, CD86, CD19, CD4, CD45R, CD152, CD138, CD8, NK1.1, CD27, CD206, CD25, CD14, CD11c, CD49b, CD34, CD69, CD123, TCRβ, CCR7, CD28, CD115, CD133, TLR4, CD117, CD79b, CD62L, CD44, CD45RA, CD1d, IAIE, CD5, and CD11b. All antibodies were conjugated using the MAXPAR reagent (Fluidigm Inc.), with Rhodium and Iridium intercalators used to identify live/dead cells. Cells were washed twice with PBS, fixed in 1.6% formaldehyde (Sigma-Aldrich, St. Louis, Mo.) for 1 hour, washed again in ultrapure H2O and subjected to CyTOF mass cytometry analysis on a CyTOF I machine, with cell events acquired at approximately 500 events per second. In addition, each sample was spiked with internal metal isotope bead standards, which then was used for sample normalization by CyTOF software (Fluidigm). Acquired data was then uploaded to a Cytobank web server (Cytobank Inc.) for data processing and gating out of dead cells and normalization beads. Data was transformed using an arcsinh(X/5) transformation.

Citrus Analysis of CyTOF Data

Differences in cell subset abundance and functional marker expression between VTA activated and control mice, were identified using the Citrus algorithm, a clustering and differential detection algorithm especially suited for high dimensional cytometry data (2). Twenty FCS files of normalized, live cell/no beads samples (Five VTA activated mice spleens, five VTA activated mice blood samples, 5 control mice spleen and five control mice blood) were each randomly sampled for 40,000 single cell events each. Briefly, Citrus performs three steps to identify cell subsets and differences between groups: First, collected single cell events are pooled together and iteratively hierarchically clustered using a subset of the measured channels for clustering (See Table 1 for a list of 23 clustering markers), yielding overlapping clusters with the ultimate cluster being one encompassing all sampled events. Second, the pooled dataset is split back into its constituting samples and the relative abundance of cells in each cluster is computed, as well as the median values of each functional marker (see Table 1 for a list of functional markers). Only cell clusters whose total abundance in one or more of the measured samples was greater than 1% of the total measured sample was retained for downstream analysis, yielding a total of 151 clusters. Third, the Citrus implementation of the SAM algorithm was applied, to identify, separately, differences in cell subset abundances and medians between VTA activated and control mouse samples at a predetermined FDR of 5%. Beyond this, an additional criteria for calling differences was employed, by performing a Mann-Whitney non-parametric test of significance on each cluster found to be different between VTA activated and control and requiring that it meet a p-value <0.05 criteria. Manual inspection of Citrus output was used to identify the closest known gross-cell type, matching the 23 combination clustering marker panel. A similar procedure analysis procedure was performed for 6-OHDA samples versus control. The analysis was focused on CD45+ cells and characterized the cell clusters using standard cell-subset definitions (B-cells, CD45R+, CD79+), plasma cells (CD45R+, CD79+, CD138+), CD8 T-cells (TCRb+, CD8+), CD4 T-cells (TCRb+, CD4+) NK cells (NK1.1+, CD49b+), granulocytes (CD11b+, Gr1+), monocytes/macrophages (CD11b+, CD14+, F4/80+).

Measurement of Cytokine Levels

VTA-activated and control mice were treated with CNO. Twenty four hours later, they were anaesthetized with ketamine/xylazine and their blood was collected by cardiac puncture. The blood was allowed to clot at room temperature for at least 30 minutes. Serum was collected by centrifuging the sample at 400 g for 10 min. The serum samples pooled from each experimental group (VTA-activated group and control group) were analyzed for cytokine and chemokine levels using the RayBio custom G-Series mouse cytokine antibody array kit (RayBiotech; Norcross, Ga.) according to manufacturer's instructions. The panel included: CD30 ligand, Eotaxin-1, Eotaxin-2, IFN-γ, IL-1α, IL-1β, IL-2, IL-3, IL-4, IL-6, IL-9, IL-10, IL-12 p40/p70, IL-12 p70, IL-13, IL-17A, MIP-1α, MIP-1γ, RANTES and TNFα. Murine IL-4 and IL-1β standard ELISA kits (PeproTech; Rocky Hill, N.J.) were used as a quantitative validation of the IL-4 and IL-1β levels measured with the antibody array kit.

In-Vitro *E. coli* Killing Assay

To evaluate the anti-bacterial efficiency of the spleen monocytes, an in-vitro killing assay was performed. Splenocytes from VTA-activated and control mice were extracted 24 hour after IP injection of CNO. Splenocytes underwent a monocyte enrichment negative selection procedure using the EasySep mouse monocyte enrichment kit (Stem-Cells Technologies, Vancouver, Canada). Enriched monocytes co-cultured with *E. coli* bacteria at a 12:1 ratio, in RPMI medium containing 10% feotal bovine serum, and incubated at 37° C. for 4 h. Monocytes were then lysed by adding 0.1% Triton X-100 (Sigma-Aldrich, US), and the lysates were diluted ×1000 in PBS. The diluted media were plated onto agar petri dishes, which were then incubated overnight at 37° C. Twelve hours later, the number of remaining bacteria colonies was counted.

In-Vivo *E. coli* Phagocytosis

Virus-injected mice were IP treated with CNO. Twenty four hours later, GFP-expressing *E. coli* (MG165K12; $8 \times 10^8$ CFU/mouse) were injected IP. After two hours, the peritoneal lymphocytes were collected by peritoneal lavage. For peritoneal lavage, the mice were sacrificed and their skin was cleaned with 70% ethanol. Then, 5 ml ice-cold PBS containing 1% fetal bovine serum were injected into the peritoneum, followed by gentle massage to allow distribution of the lavage fluid throughout the peritoneal cavity. The fluid was then collected using a 5 ml syringe attached to a 21-guage needle, and cells were then washed twice in FACS staining buffer (PBS containing 1% bovine serum albumin and 0.05% sodium azide). In order to evaluate the degree of monocyte phagocytosis of the fluorescent bacteria, peritoneal lavage cells were stained with PerCP-conjugated anti-CD11b antibody (M1/70, Biolegend). All samples were analyzed on an LSRFortessa cell analyzer (BD Biosciences, NJ). Data analyses were performed using FACSDiva software (BD Biosciences, NJ).

Sympathetic Denervation

Virus-injected mice (30 days after stereotactic injection) were sympathetically denervated by two IP injections of 6-OHDA (150 mg/kg in 0.01% ascorbic acid, Sigma-Aldrich, St. Louis, Mo.) administered at 24 h intervals. Mice were injected IP with CNO five days after the last 6-OHDA injection. Twenty four hours after the CNO injection, spleens were removed for CyTOF analysis and in vitro *E. coli* killing assay.

Statistical Analysis

Analysis of CyTOF data is described in the Citrus analysis of CyTOF data section. Significance levels of other data were determined using Prism5 (GraphPad Software, La Jolla, Calif.). Experiments were analyzed by two-tailed Student's t-test or by one-way or two-way analysis of variance (ANOVA), as indicated for each experiment.

Example 1: Regulating Neuronal Activity (Designer Receptors Exclusively Activated by Designer Drugs (DREADDs and Optogenetics)

Tyrosine hydroxylase (TH)-Cre transgenic mice EM:00254 (European Mutant Archive) were bred at the Technion's animal housing facility. All animal protocols were performed in accordance with the National Institutes of Health Guide for Care and Use of Laboratory Animals.

Causal Effect of the VTA DA Neurons on the Immune System

Figure 2:
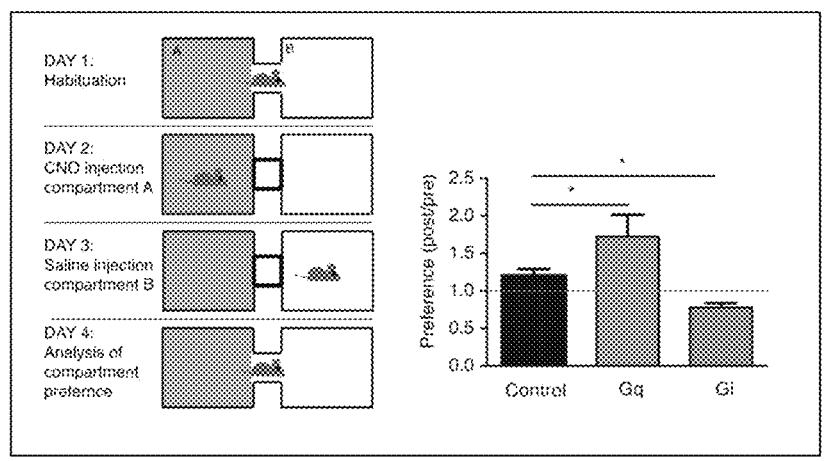
FIG. 2. Includes a scheme and a bar graph showing the VTA DA neurons activation or inhibition response in the CPP paradigm. (A) Three groups of mice are used in this experiment: mice injected with AAV virus encoding the hM3D (Gq), hM4D (Gi) or control carrying only mCherry. On day 1 the mice are given a chance to explore the apparatus for 5 minutes. Day 2: the mice are injected with CNO (2.5 mg/kg), which activates, inhibits or does not affect the VTA DA neurons (depends on the type of DREADD they express). At this stage the mice were only allowed access to one compartment of the apparatus and remains in the compartment for 30 minutes. Day 3: Mice were confounded to the other compartment. They are injected with saline and remain in this compartment also for 30 minutes as well. Day 4: In the preference testing phase the animal is allowed barrier free access to all compartments of the apparatus. Time spent in each compartment is measured by motion detecting software (EthoVision). The Gq mice exhibited a preference for the conditioned chamber. The Gi mice avoided the conditioned chamber. Fold change in time in conditioned chamber during day 4 versus day 1 of the CPP is defined as preference. $P<0.05$ for one way ANOAVA; followed by Dunnett's multiple comparisons test (n=4) (bar graph).
Figure 4:
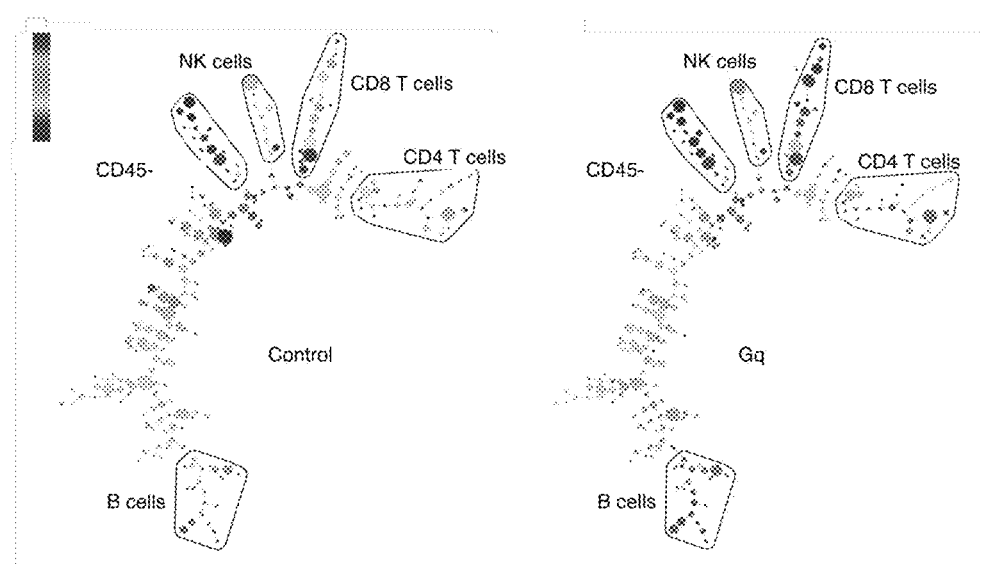
FIG. 4. Is an intensity representation of recorded effects of VTA dopamine activation on CD62L (L-selectin) expression in CD8 T cells. Spleens were collected from control and Gq mice 24 h after VTA DA activation and LPS injection. The cells were analyzed as described in FIG. 4. Of note, here the nodes are colored by intensity of specific marker (CD62L) expression within the defined population. As one can see a significant change was evident in the CD8 population.

The data presented herein establishes the causal effect of the VTA DA neurons on the immune system and validated the ability to execute the proposed experiments. Expression of the virus in the VTA TH positive cells (FIG. 1). CNO injection resulted in behavioral effect in the CPP paradigm in mice injected with the activating DREADD (Gq) and mice injected with inhibiting DREADD (Gi) (FIG. 2). Some of the effects of VTA dopamine activation on the immune response to LPS are shown in FIGS. 3-4. The analysis was done using high-throughput technology CyTOF and was also validated for specific markers with standard FACS assay. Following LPS stimulation significant changes in the number of NK cells, monocytes and B-cells (FIG. 3) were recorded. No change was detected in the levels of CD69, a general activation marker.

The CyTOF analysis also revealed changes in CD8 T cells (FIG. 4). This effect is surprising because CD8+ T cells do not express receptors to LPS and therefore cannot be stimulated by it directly. These effects represented a complex modulation of the immune response via VTA's activation.

Figure 5:
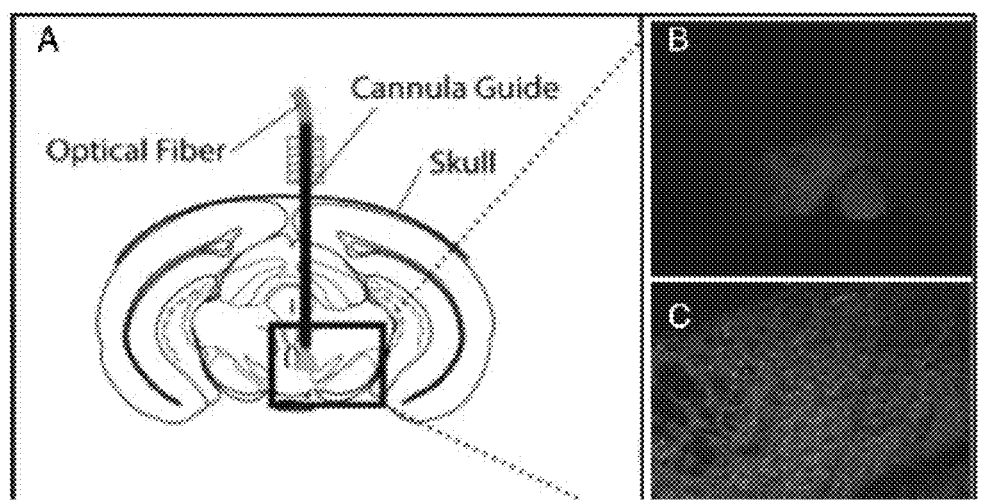
FIGS. 5A-5C. Includes a map and two micrographs showing the expression of ChR2 (an activating channel responsive to light) in the VTA. Specific ChR2 expression in DA neurons.

These findings demonstrate the potential of CyTOF analysis in identifying unpredictable effects. This is especially important when analyzing the communication between two highly complex systems. To manifest this capacity to execute the experiments that require optogenetic manipulation, FIG. 5 depicts the site of virus injection cannula placement and expression of ChR2-encoding virus in the VTA.

Viral-mediated gene transfer and stereotaxic surgery: Cre-dependent AAV (EF1-alpha promoter) viruses purchased from the University of North Carolina vector core facility (UNC), were used to express hM3Dq (Gq DREADDs) or hM4Di (Gi). Control virus contained only the fluorescent marker without the DREADD information. Before virus injection, mice were be anaesthetized with a ketamine (100 mg/kg) and xylazine (10 mg/kg) mixture and placed in a stereotaxic apparatus (Stoelting). The viruses were injected using 33-gauge needle placed unilaterally into the VTA (anterior-posterior, −3.3 mm; lateral-medial, +0.5 mm; dorsal-ventral, −4.4 mm (mouse coordinates)). The virus (0.5 µl) was infused at a rate of 0.1 µl/min. Four weeks were allowed for recovery and virus expression. Analysis of cell-expressing viruses was performed by immunohistochemistry at the end of the experiments. Mice were screened for the functional effect of DREADD manipulation, using conditioned place preference paradigm (See FIG. 2). Mice that fail to manifest any behavioral effect were excluded from analysis.

Behavioral analysis (conditioned place preference; CPP): Three groups of mice were used in this experiment: mice injected with AAV virus encoding the hM3D (Gq), hM4D (Gi) or control carrying only mCherry. On day 1 the mice were given a chance to explore the apparatus for 5 minutes. Day 2: the mice were injected with CNO (2.5 mg/kg), which activates, inhibits or does not affect the VTA DA neurons (depends on the type of DREADD they express). At this stage the mice were only allowed access to one compartment of the apparatus and remains in the compartment for 30 minutes. Day 3: Mice were confounded to the other compartment. They were injected with saline and remained in this compartment for 30 minutes as well. Day 4: In the preference testing phase the animals were allowed barrier free access to all compartments of the apparatus. Time spent in each compartment was measured by motion detecting software (EthoVision). The Gq mice exhibited a preference for the conditioned chamber. The Gi mice avoided the conditioned chamber. Fold change in time in conditioned chamber during day 4 versus day 1 of the CPP was defined as preference (See FIG. 2).

Immunity analyses: High-throughput analysis is used to identify the main changes in the immune system.

CyTOF mass cytometry: Single-cell suspensions of cells from the blood/bone marrow/spleen/lymph nodes of the treated mice are stained with monoclonal or polyclonal antibodies, conjugated to metal probes. The staining panel constitutes of 33 antibodies in designed to identify all major cellular subsets including effector CD4+ T, effector memory CD4+ T, central memory CD4+ T, activated CD4+ T, effector CD8+ T, effector memory CD8+ T, central memory CD8+ T, Tregs, plasmacytoid DC, myeloid DC, erythrocytes, macrophages, monocytes, B-cells, NK cells and granulocytes.

Flow cytometry analysis: Cells are stained with monoclonal or polyclonal antibodies, conjugated to fluorescent dyes such as fluorescein isothiocyanate (FITC), phycoerythrin (PE), allophycocyanin (APC), pacific blue (PB). Using this technique, changes in the specific populations identified in the CyTOF analysis are monitored. Analysis is performed using the FlowJo program.

Cytokines analysis: For the initial high-throughput screening, Luminex is used to identify changes in tens of cytokines in the serum of mice from the different experimental groups. Luminex is a bead-based assay system, in which beads of defined spectral properties are conjugated to protein-specific capture antibodies. The beads are analyzed with a Luminex detection system and the concentration of one or more proteins can be determined. For analysis of specific cytokines, commercially available ELISA assays are utilized according to the manufacturer's instructions. Additional specific assays are used to examine the functional effects of reward circuit manipulation on specific cell populations. These include standard assays: transwell migration assay, for studying the motility of immune cells. Clonogenic Assay or colony formation assay is an in vitro cell survival assay based on the ability of a single cell to grow into a colony.

Statistics: To account for possible differences in the viral infection efficiency, at least 6 mice are included in each experimental group (based on power analysis with $\alpha=0.05$, $\beta=0.2$). CyTOF: the statistical analysis of the data is performed within a defined population to determine changes in intensity of specific markers using single cell event distributions, or between populations using non-paramteric tests of differences as well as ratio tests. Samples for Luminex analysis are run in duplicate and the analysis conducted through SAXcyB, a dedicated Luminex analysis algorithm using the full distribution of bead intensities.

Figure 6:
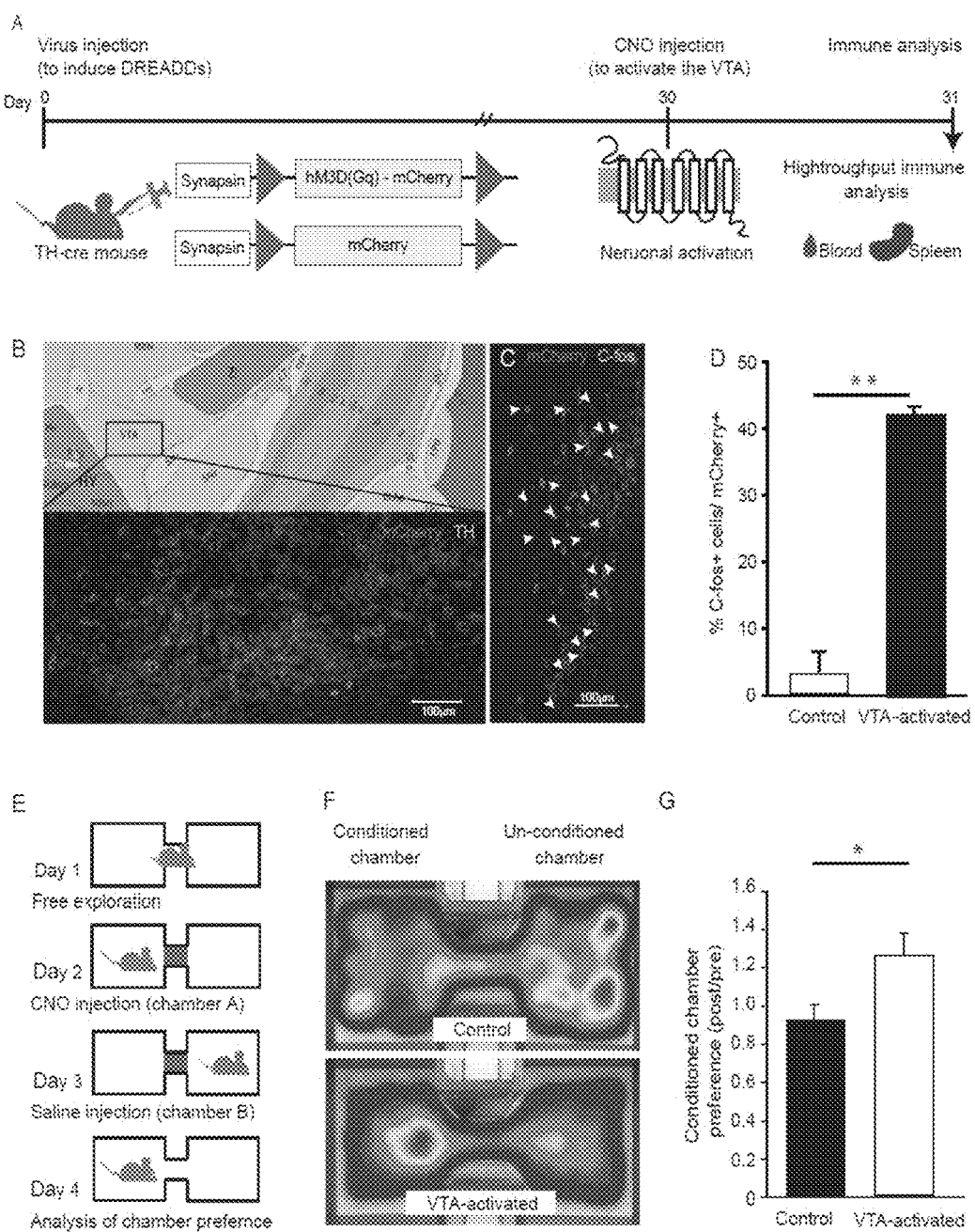
FIGS. 6A-6G. Demonstrates the DREADD-mediated activation of VTA dopaminergic neurons system.

Example 2: Dopaminergic Neurons in the Ventral Tegmental Area (VTA) Regulate Immunity The ability of dopaminergic neurons in the ventral tegmental area (VTA) in regulating immunity was assessed. Exclusively Activated by Designer Drugs (DREADDs) were used to activate these neurons and then broadly characterized subsequent immune responses (FIG. 6A). Unlike traditional brain manipulation techniques, this pharmacogenetic approach enables cell-specific and location specific targeting of neurons in order to establish causal relationships with a measured phenotype. AAV8 virus was used to achieve expression of the activating form of DREAADs and the fluorescent reporter, mCherry (hM3D(Gq)-mCherry), in the VTA dopaminergic neurons of tyrosine hydroxylase (TH)-cre mice. As control, another group of mice was infected with a sham virus containing the information for the fluorescent marker but lacking the information for DREADDs (FIG. 6A).

Efficiency of the viral infection in the dopaminergic (TH+) VTA neurons was 58±4% (FIG. 6B). Neurons expressing DREADDs were activated by systemic injection of clozapine-N-oxide (CNO 2.5 mg/kg; CNO does not convert to clozapine in mice). Of note, CNO was injected to mice in both groups. Neuronal activation was determined by C-fos staining, an immediate early activation marker. C-fos expression was observed in 42±0.5% of the DREADDs-infected cells compared to 3±1% in the control mice (FIG. 6C-D). To validate the rewarding effect of VTA dopaminergic neuron activation, conditional place preference paradigm (CPP) was used, which is a behavioral test that quantifies an animal's preference towards a chamber in which it had a positive experience (see Methods; FIG. 1E). The CPP analysis revealed that mice in the VTA-activated group showed an increased preference to the conditioned chamber in which they were injected with CNO to induce VTA-activation (FIG. 1E-G; $p<=0.042$). Mice in the control group showed no such bias. These findings indicate that DREADDs were specifically expressed on VTA dopaminergic neurons and that their activation induced a positive experience.

Next, to test the hypothesis that activation of the VTA dopaminergic neurons affects immunity, mice were injected with CNO and their blood and spleen were collected 24 hours (h) thereafter. To capture and evaluate immune capabilities, the high dimensional immune phenotyping capabilities of mass-cytometry were used.

Figure 7:
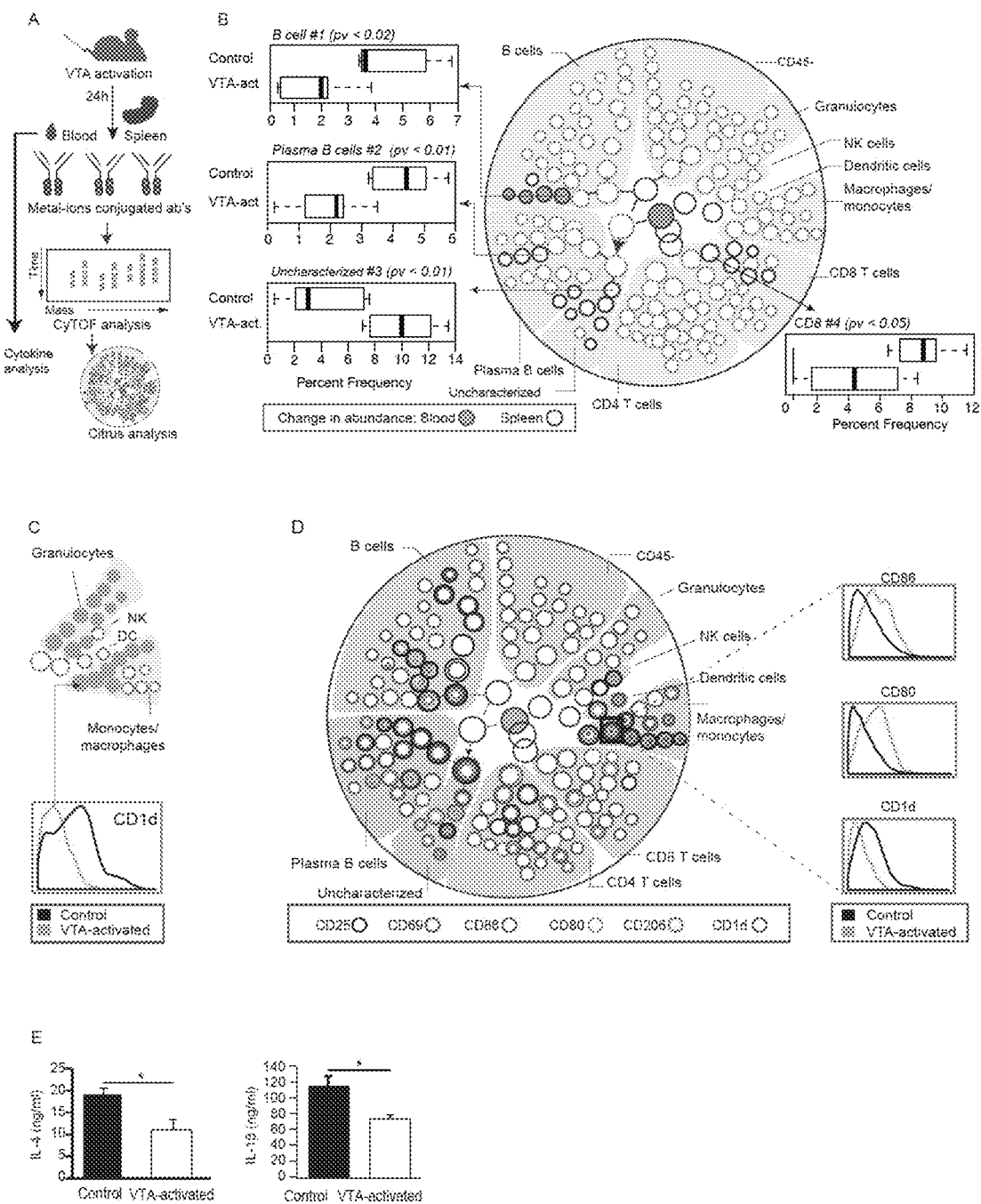
FIGS. 7A-7E. VTA dopaminergic neuron activation induced broad but specific changes in immune populations.

(CyTOF) simultaneously measured 36 antibodies for cell-surface markers at the single cell level (FIG. 7A and Table 1). To analyze the data, Citrus, a dedicated high dimensional cytometry clustering algorithm was used, to identify clusters of cells with high similarity of expression in 23 of these markers (clustering antibodies), indicative of cell-type (See Materials and Methods). The analysis yielded 151 hierarchically organized cell clusters. Clusters were then each annotated using standard cell-subset definitions (B-cells: CD45R+, CD79b+; plasma cells: CD45R+, CD79b+, CD138+; CD8 T-cells: TCRb+, CD8+; CD4 T-cells: TCRb+, CD4+; NK cells: NK1.1+, CD49b+; granulocytes: CD11b+, Gr1+; monocytes/macrophages: CD11b+, CD14+, F4/80+ or an "Uncharacterized"cluster of cells expressing a combination of markers). Thus, by monitoring differences in cell clusters between the two treatment groups (VTA-activated and control mice), it was possible to capture a systems view of the cellular changes in the immune system.

TABLE 1

| Antibody | Channel | Clone |
|---|---|---|
| Clustering markers | | |
| CD45 | 115In | 30-F11 |
| CCR3 | 139La | JO73E5 |
| GR1 | 142Nd | RB6-8C5 |
| F4/80 | 144Nd | BM8 |
| CD4 | 145Nd | RM4-5 |
| CD45R | 146Nd | RA3-6B2 |
| CD138 | 148Nd | 281-2 |
| CD8 | 149Sm | 53-6.7 |
| NK1.1 | 150Nd | PK136 |
| CD206 | 151Eu | C068C2 |
| CD14 | 153Eu | Sa14-2 |
| CD11c | 154Sm | N418 |
| CD49b | 156Gd | DX5 |
| CD34 | 158Gd | MEC14.7 |
| CD123 | 161Dy | 5B11 |
| TCRβ | 162Dy | H57-597 |
| CCR7 | 163Dy | 4B12 |
| CD115 | 165Ho | AFS98 |
| CD133 | 166Er | 315-2C11 |
| CD79B | 169Tm | HM79-12 |
| CD45RA | 173Yb | 14.8 |
| CD5 | 175Lu | 53-7.3 |
| CD11b | 176Yb | M1/70 |
| Functional markers | | |
| CD80 | 141Pr | 16-10A1 |
| CD86 | 143Nd | GL-1 |
| CD152 | 147Sm | 9H10 |
| CD25 | 152Sm | 3C7 |
| CD27 | 159Tb | LG.3A10 |
| CD69 | 160Gd | H1.2F3 |
| CD28 | 164Dy | 37.51 |
| TLR4 | 167Er | SA14-21 |
| CD117 | 168Er | ACK2 |
| CD62L | 170Er | MEL-14 |
| CD44 | 171Yb | IM7 |
| CD1d | 172Yb | K253 |
| IA/IE | 174Yb | M5/114.15.2 |

The CyTOF screen revealed broad changes in the relative abundance of several cell clusters in the blood and spleen of VTA-activated mice compared to controls (false discovery rate; FDR threshold of 5%). Specifically, B-cell subsets in both blood and spleen showed a decreased in abundance, as did plasma B-cells and CD8+ T-cells in the spleen (FIG. 7B). In parallel to these changes, were observed as a reciprocal increase in a set of cell clusters that expressed high levels of B220+, CD79b+ and CD138+, but were also positive for NK1.1, CD14, CD115, CD133 and CD34 (uncharacterized), making it difficult to interpret the biological significance of their increase in abundance.

Next, to capture the broad effects of VTA-activation on immune system function, the expression of 13 functional markers (Table 1) on each cell cluster between VTA-activated and control mice, were compared. In the blood, differences in expression of only a single marker, namely CD1d (FIG. 7C) were noted. CD1d levels were reduced in multiple antigen presenting cell (APC) subsets, including granulocytes, NK cells and monocyte/macrophages but not on B-cells. CD1d is a glycoprotein, structurally resembling WIC class I, which presents glycolipid antigens, specifically to NKT cells and may thus represent a potential regulation of the NKT population. In contrast to the limited differences in functional markers expression between the two groups in the blood, the differences in the spleen were more pronounced.

These were evident both in the number of cell clusters showing differences in functional marker expression and in the number of functional markers affected (FIG. 7D). Of note, the direction of change (increase or decrease) of functional marker was similar, in all cell clusters, indicative of a system wide coherent behavior: Upregulation of CD80 and CD86, downregulation of CD1d and upregulation of CD25, CD69 and CD206 were also recorded. These changes were mostly evident on APCs, including B-cells, NK and dendritic cells (DC) and were most profound on monocyte/macrophages. With the latter showing the biggest effect size differences and in multiple functional markers; including the CD80, CD86 and CD1d, molecules related to antigen presentation (FIG. 7D inset), the activation markers CD25, CD69 and the mannose receptor, CD206, which is associated with phagocytic activity. In addition to APCs, changes were observed on CD4+ T cells, specifically an increase in CD25 and CD206 on these cells.

Figure 10:
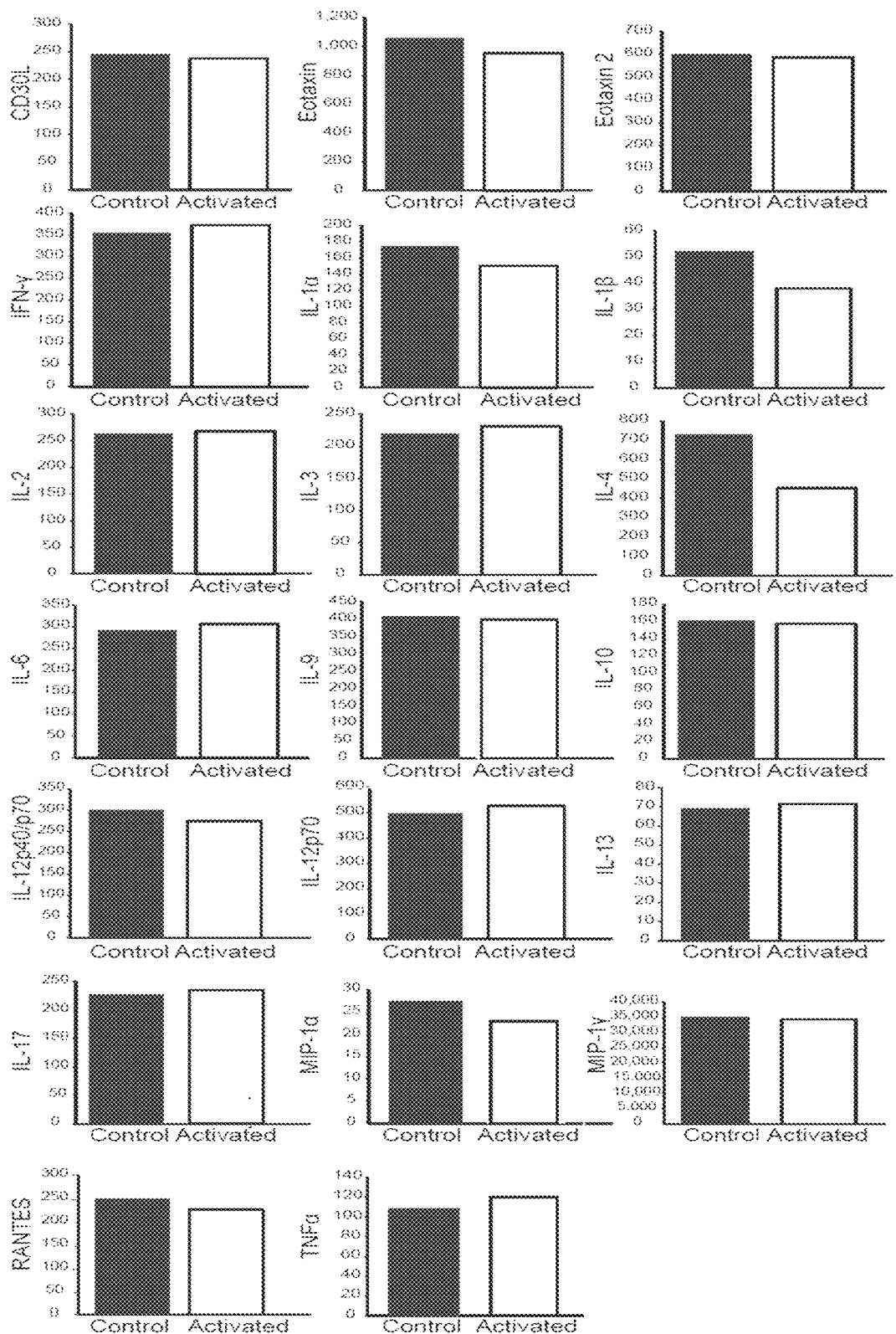
FIG. 10. RayBio mouse cytokine antibody array results. Bar graphs of Serum samples of VTA activated and control mice were analyzed for their cytokines levels using RayBio. Raw data was analyzed with the RayBio Analysis Software and for each cytokine measured in the array, numeric fluorescent intensities are reported. The results are reported following the background fluorescence subtraction and normalization. The data was obtained from pooled three mice pooled for each group.

To complement the cellular analysis by CYTOF, the serum cytokine levels changes following VTA activation using the RayBio antibody array, were monitored. Of the 20 tested cytokines, only the levels of IL-4 and IL-1β, key anti-inflammatory and pro-inflammatory cytokines, respectively, were significantly reduced (FIG. 7E and FIG. 10, ELISA validation for IL-4 and IL-1β; IL-4: $P<=0.045$; IL-1β3: $p<=0.041$). Taken together, the broad immune screen performed showed multiple, cell-specific, alterations, potentially priming the immune system.

To test for functional changes in immune activity following VTA activation, monocytes/macrophages were assayed (the most profound changes in the CyTOF screen). Due to the increase in CD206 levels on these cells, their phagocytic capacity was examined. Cd11b+,Ly6G-cells were isolated from the spleens of both VTA-activated and control mice 24 h following CNO injection. Cells were cultured with E. coli for four hours and then lysed.

Figure 8:
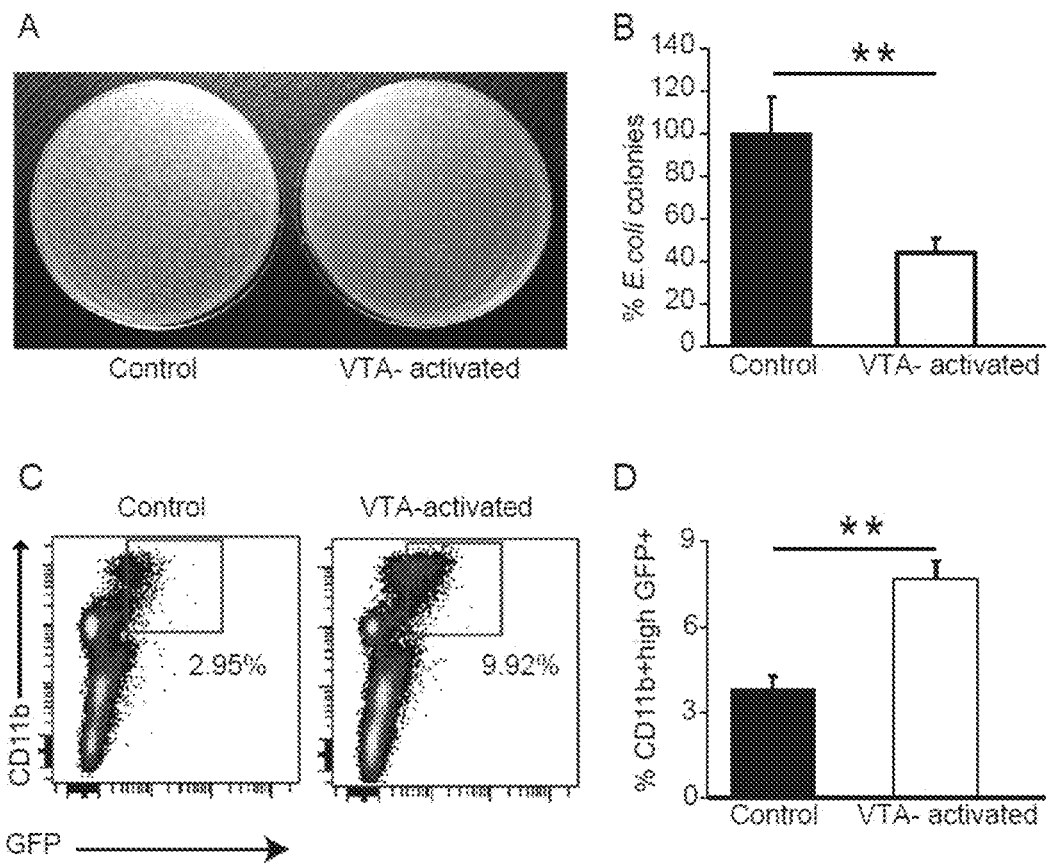
FIGS. 8A-8D. Activation of VTA dopaminergic neurons increases antibacterial and phagocytic activity of monocytes/macrophages. Monocytes/macrophages were isolated from the spleens of mice 24 h following activation of VTA dopaminergic neurons were co-cultured ex-vivo with *E. coli* for four hours. The cells were lysed and the remaining media was plated on agar to evaluate the number of remaining bacteria.

The remaining media was plated on agar plates and counted the remaining bacteria colonies. A significant decrease in the number of remaining E. coli colonies in the cultures that were incubated with cells from VTA-activated mice was measured when compared to controls ($p<-0.026$; FIG. 8A,B). These findings indicate that activation of the VTA dopaminergic neurons increased the antibacterial capacity of monocytes/macrophages.

To determine the effects of VTA activation on antibacterial activity in vivo, the VTA-dopaminergic neurons were activated, and 24 h later injected the mice with GFP-expressing E. coli. Two hours later, lymphocytes were extracted from the peritoneal cavity of the mice and determined by flow cytometry GFP levels; only cells that phagocytized the E. coli could express GFP. VTA-activated mice had an increased number of CD11b+GFP+ cells in the peritoneum when compared to controls ($p<=0.003$; FIG. 8C, D).

Figure 9:
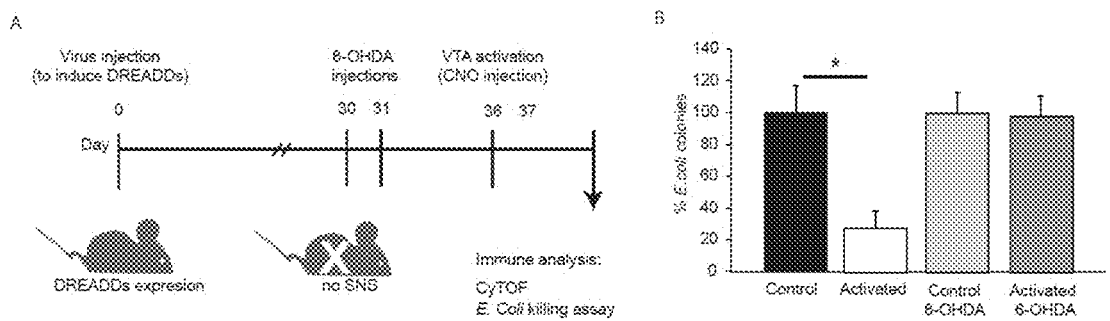
FIGS. 9A-9B. Effects of VTA dopaminergic neurons activation on the immune system require functional sympathetic nervous system.
Figure 11:
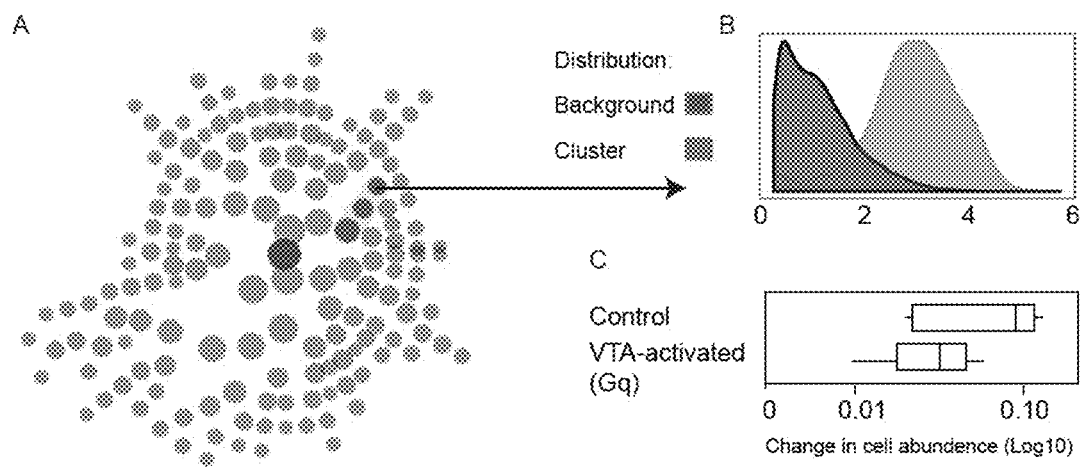
FIGS. 11A to 11C. Changes in the immune system following VTA activation sympatheticallyablated mice.

These findings demonstrate that the immunological antibacterial capacities increased following VTA-activation. Moreover, this manipulation of the VTA has been shown to impact SNS activity. To determine if the SNS was involved in mediating the effects of DREADDs-driven VTA activation on the immune system, 6-hydroxydopamine (6OHDA) was IP injected to chemically ablate peripheral catecholaminergic neurons comprising the SNS (6OHDA does not cross the blood brain barrier). Five days after injection, the VTA-dopaminergic neurons were activated and 24h later, spleenocytes were isolated for analysis using CyTOF (FIG. 9A). In the absence of an intact SNS, there was no impact to the VTA-activation on the immune system (CD45+ cells) and no significant differences were detected between the two mouse groups (FIG. 11, q-value$<=0.1$). Accordingly, whereas in mice whose SNS was intact, the activation of the VTA increased the antibacterial capacity of the monocytes/macrophages, in the 6OHDA-treated mice, the antibacterial activity of monocytes/macrophages derived from VTA-activated mice, was similar to that observed in controls (FIG. 9B).

Figure 14:
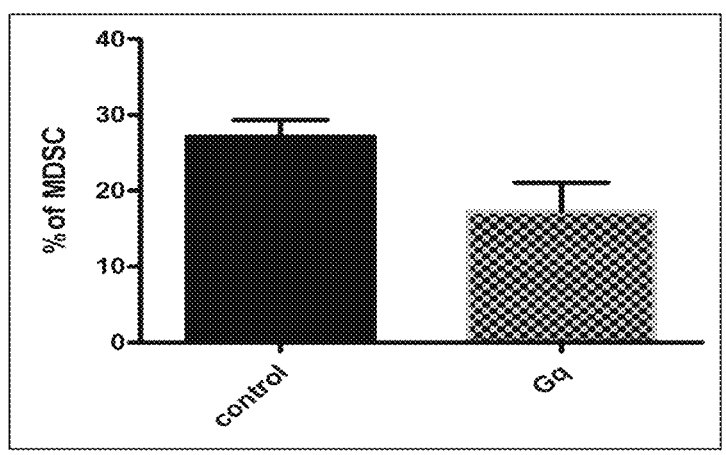
FIG. 14. A bar graphs showing the reduced abundance of MDSCs in the tumor after VTA dopaminergic neurons activation. CNO was injected daily for two sessions of three days each (separated by seven day interval; total of six days). CNO injections started immediately with the injection of tumor cells. The abundance of MDSCs in the tumor was determined and presented as % of total cells. Student's t-test p=0.05. (n=5 per group).
Figure 15:
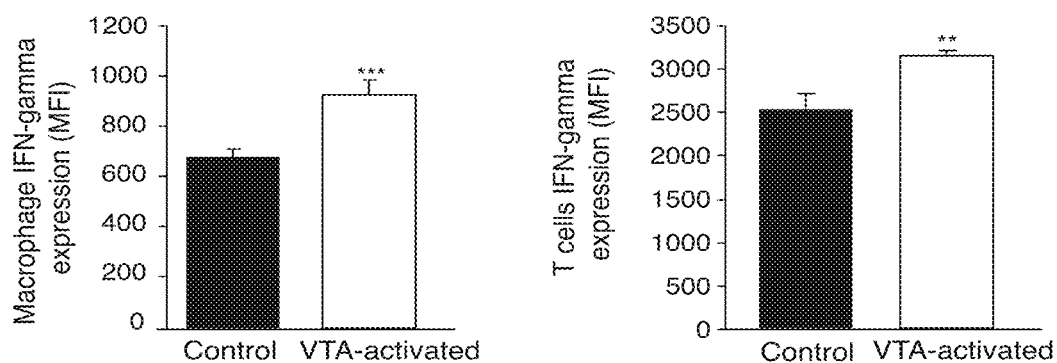
FIG. 15. Bar graph showing the elevation in immune potent macrophages and T-cell upon in-vivo microbial immune induction in accordance with example 2.
Figure 16:
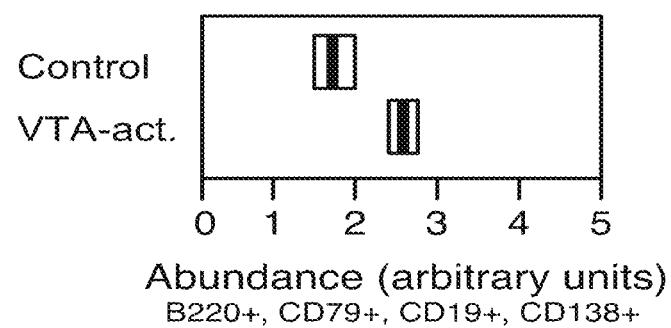
FIG. 16. A boxplot showing the elevation in immune potent B-cells upon in-vivo microbial immune induction in accordance with example 2.

Thus, the present data indicates that the signal from the brain's reward system is mediated, at least in part, via the SNS. In conclusion, Using the present approach it was demonstrated that direct activation of the VTA dopaminergic neurons, a key component of the reward system, critically and surprisingly affects immunity. The effects are profound and include changes in multiple arms of the immune system including B-cells, granulocytes, NK, dendritic cells and monocytes/macrophages following the activation of the VTA-dopaminergic neurons. Last, in-vivo induction of the immune system together with VTA neuronal stimulation resulted in increase in the amount of T-cells and macrophages expressing another activation marker-interferon gamma (FIG. 14). Likewise, B-cells in microbially challenged animals treated with VTA neurons inducer displayed elevated amounts of B-cells expressing B220, CD79, CD19, and CD 138 (FIG. 15).

Due to the fact that monocytes/macrophages demonstrated the most significant change in functional markers these cells were the focus of the study. It is important to emphasize that the effects described in this study were all initiated by direct manipulation of the VTA dopaminergic neurons and involved the SNS.

Example 3: Activation of Dopaminergic Neurons in the Ventral Tegmental Area (VTA) Inhibit Melanoma and Lung Carcinoma In these experiments, the ability of treating cancer by activating neurons in the VTA was tested. Two cancers were selected: solid melanoma (B16) tumor and Lewis lung carcinoma (LLC). Activating neurons in the VTA surprisingly resulted in over 40% reduction in tumor size when compared to control mice. Moreover, activating neurons in the VTA resulted in a significant reduction in the abundance and cell surface markers expression of CD11b+ Gr1+

Myeloid Derived Suppressor Cells (MDSCs). These effects were evident in the spleen, bone marrow and in the tumor.

Methods

For the expression of DREADDs, injected Cre-dependent adeno-associated virus (AAV) vector expressing DREADDs fused with red fluorescent protein mCherry, was injected into the VTA of tyrosine hydroxylase (TH)-Cre transgenic mice.

Control mice: demonstrate the independent effects of the surgical procedure, virus injection and CNO exposure on the immune system. Then the mice were challenged with 500×$10^3$ LLC cells (Lewis Lung carcinoma Cells) or 200×$10^3$ B16 melanoma tumor cells (gently injected subcutaneously into the middle right flank of each animal).

Figure 12:
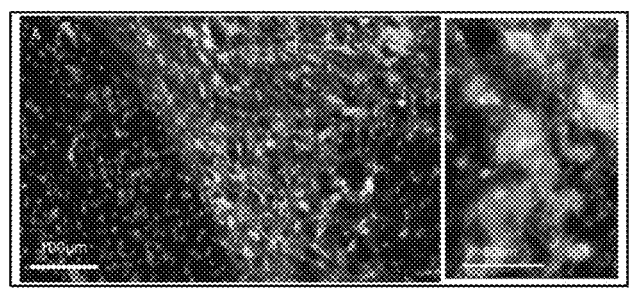
FIGS. 12A-12B. Micrographs showing the specificity of virus expression in TH+neurons of the VTA. 12A show Cre-dependent AAV (expressing hM3D(Gq)-mCherry) was injected into the VTA. Fluorescent microscope image of an injected slice demonstrates colocalization of mCherry expression with the TH antibody, costained with 4",6"-diamidino-2-phenylindole (DAPI).

The VTA of these mice was activated for four days a week for the duration of tumor growth. 28 days from the tumor cells injection a group of the tumor-bearing animals were euthanized to dissect the tumor tissue and check for metastasis (FIG. 12). The spleen bone marrow and tumors were isolated to characterize the changes in immune cells. The CyTOF was used to analyze the immune system as well as FACS analysis.

Figure 13:
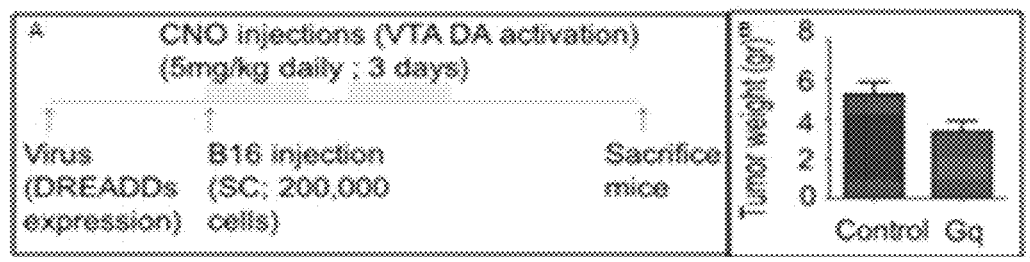
FIGS. 13A-13B. Reduced tumor size (B16 melanoma), after VTA dopaminergic neurons activation.

The results (see also FIGS. 12-14) indicate that melanoma and carcinoma progression was inhibited and clear cancer regression signs were recorded following VTA activation. Moreover the actual tumor size was dramatically and unexpectedly reduced (FIG. 12).

Interestingly, VTA dopaminergic neurons activation also clearly reduced the abundance of MDSCs in the tumor. These clear indications prove that activation of VTA dopaminergic neurons actually cure and reverse at least two types of cancer.

The invention claimed is:

1. A method for inducing an immune response in a subject in need thereof, comprising the step of directly activating dopaminergic neurons in the ventral tegmental area (VTA) of said subject by magnetic stimulation so as to increase the activity, the abundance or both, of at least one cell selected from the group consisting of: a natural killer cell (NK), a CD8 T-cell, a CD4 T-cell, a B-cell, a dendritic cell, a macrophage, a granulocyte, or any combination thereof, thereby inducing an immune response in the subject in need thereof.

2. The method of claim 1, wherein said increased activity, abundance or both, of at least one cell selected from the group consisting of: a natural killer cell (NK), a CD8 T-cell, a CD4 T-cell, a B-cell, a dendritic cell, a macrophage, a granulocyte, or any combination thereof comprises increased level, abundance, or both, of CD62L in CD8 T-cells, CD1d in granulocytes, CD1d in macrophages, CD206 in B-cells, CD206 in $CD8^+$ T-cells, CD80 in macrophages, CD86 in B-cells, CD69 in macrophages, CD25 in B-cells, interferon gamma in T-cells, interferon gamma in macrophages, B220 in B-cells, CD79 in B-cells, -CD138 in B-cells, CD19 in B-cells or any combination thereof.

3. The method of claim 1, wherein said activating is applying said magnetic stimulation to the following coordinates: 0 to 5; −17 to −13; and −12 to −8.

4. The method of claim 1, further comprising a step of determining an increased activity, abundance, or both, of at least one cell selected from the group consisting of: a natural killer cell (NK), a CD8 T-cell, a CD4 T-cell, a B-cell, a dendritic cell, a macrophage, a granulocyte, or any combination thereof, in a sample obtained from said subject.

5. The method of claim 1, wherein said inducing is increasing the number of NK cells, B-cells, dendritic cells, macrophages, granulocytes, or any combination thereof, in the spleen of said subject.

6. The method of claim 1, further comprising a step of determining an increased level, abundance, or both, of CD62L in CD8 T-cells, CD1d in granulocytes, CD1d in macrophages, CD206 in B-cells, CD206 in $CD8^+$ T-cells, CD80 in macrophages, CD86 in B-cells, CD69 in macrophages, CD25 in B-cells, interferon gamma in T-cells, interferon gamma in macrophages, B220 in B-cells, CD79 in B-cells, CD138 in B-cells, CD19 in B-cells or any combination thereof, in a sample obtained from said subject.

7. The method of claim 1, wherein said immune response comprises targeting: a pathogen, a foreign cell or a molecule, a neighboring cell, an abnormality, or a combination thereof.

8. The method of claim 7, wherein said targeting comprises engulfing, destructing, or both.

9. The method of claim 7, wherein said neighboring cell is infected by a virus.

10. The method of claim 1, wherein said immune response is selected from the group consisting of: antibacterial activity, phagocytotic activity, or both.

* * * * *